US012599636B2

(12) United States Patent
Escolar et al.

(10) Patent No.: US 12,599,636 B2
(45) Date of Patent: Apr. 14, 2026

(54) TREATMENT OF KRABBE DISEASE WITH UMBILICAL CORD BLOOD TRANSPLANTION (UCBT) AND INCREASED GALACTOCEREBROSIDASE (GALC) EXPRESSION

(71) Applicant: University of Pittsburgh—Of the Commonwealth System of Higher Education, Pittsburgh, PA (US)

(72) Inventors: Maria Luisa Escolar, Sewickley, PA (US); Paul Szabolcs, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1000 days.

(21) Appl. No.: 16/349,514

(22) PCT Filed: Jan. 19, 2018

(86) PCT No.: PCT/US2018/014370
§ 371 (c)(1),
(2) Date: May 13, 2019

(87) PCT Pub. No.: WO2018/136710
PCT Pub. Date: Jul. 26, 2018

(65) Prior Publication Data
US 2019/0336540 A1 Nov. 7, 2019

Related U.S. Application Data

(60) Provisional application No. 62/448,433, filed on Jan. 20, 2017.

(51) Int. Cl.
| | |
|---|---|
| *A61K 39/395* | (2006.01) |
| *A61K 9/00* | (2006.01) |
| *A61K 31/17* | (2006.01) |
| *A61K 31/255* | (2006.01) |
| *A61K 31/365* | (2006.01) |
| *A61K 31/436* | (2006.01) |
| *A61K 31/7076* | (2006.01) |
| *A61K 35/51* | (2015.01) |
| *A61K 38/47* | (2006.01) |
| *A61P 25/02* | (2006.01) |
| *A61K 48/00* | (2006.01) |

(52) U.S. Cl.
CPC ........... *A61K 35/51* (2013.01); *A61K 9/0019* (2013.01); *A61K 31/17* (2013.01); *A61K 31/255* (2013.01); *A61K 31/365* (2013.01); *A61K 31/436* (2013.01); *A61K 31/7076* (2013.01); *A61K 38/47* (2013.01); *A61K 39/3955* (2013.01); *A61P 25/02* (2018.01); *C12Y 302/01046* (2013.01); *A61K 48/00* (2013.01)

(58) Field of Classification Search
None
See application file for complete search history.

(56) References Cited

U.S. PATENT DOCUMENTS

| | | | | |
|---|---|---|---|---|
| 9,986,722 B2 * | 6/2018 | Fogh | .................. | C12N 15/8509 |
| 2003/0223963 A1 | 12/2003 | Davidson et al. | | |
| 2006/0003312 A1 | 1/2006 | Blau et al. | | |

FOREIGN PATENT DOCUMENTS

| | | |
|---|---|---|
| CN | 104735976 A | 6/2015 |
| EP | 2 341 068 B1 | 9/2013 |

OTHER PUBLICATIONS

Ngo et al., 1994, The Protein Folding Problem and Tertiary Structure Prediction, pp. 492-495.*
EP 18741529.4 Extended European Search Report dated Sep. 23, 2020 (6 pages).
Gabig-Cimińska et al., "Combined Therapies for Lysosomal Storage Diseases," *Curr Mol Med.* 15:746-771, 2015.
Karumuthil-Melethil et al., "Intrathecal Administration of AAV/GALC Vectors in 10-11-Day-Old Twitcher Mice Improves Survival and is Enhanced by Bone Marrow Transplant," *J Neurosci Res.* 94:1138-1151, 2016.
Reddy et al., "Bone Marrow Transplantation Augments the Effect of Brain- and Spinal Cord-Directed Adeno-Associated Virus 2/5 Gene Therapy by Altering Inflammation in the Murine Model of Globoid-Cell Leukodystrophy," *J Neurosci.* 31:9945-9957, 2011.
Anurathapan et al., "Pharmacologic Immunoablation Followed by Reduced-Toxicity Conditioning and Stem Cell Transplantation in High-Risk Thalassemia: A Safe Approach to Disease Control," *Biol Blood Marrow Transplant.* 19:1259-1262, 2013.
Harnicar et al., "Intensified Mycophenolate Mofetil Dosing and Higher Mycophenolic Acid Trough Levels Reduce Severe Acute Graft versus-Host Disease After Double-Unit Cord Blood Transplantation," *Biol Blood Marrow Transplant.* 21:920-925, 2015.
Horwitz et al., "Myeloablative intravenous busulfan/fludarabine conditioning does not facilitate reliable engraftment of dual umbilical cord blood grafts in adult recipients," *Biol Blood Marrow Transplant.* 14:591-594, 2008.
Bradbury et al., "Natural history study and preliminary assessment of therapies in canine globoid cell leukodystrophy," *Mol Gen Metab* 117:S29, 2016. (Abstract).
Choudhury et al., "Viral vectors for therapy of neurologic diseases," *Neuropharmacol.* 120:63-80, 2017.
De et al., "High Levels of Persistent Expression of A1-Antitrypsin Mediated by the Nonhuman Primate Serotype rh. 10 Adeno-associated Virus Despite Preexisting Immunity to Common Human Adeno-associated Viruses," *Mol Ther.* 13:67-76, 2006.

(Continued)

*Primary Examiner* — Yunsoo Kim
(74) *Attorney, Agent, or Firm* — Klarquist Sparkman, LLP

(57) ABSTRACT
This application provides methods of treating Krabbe disease, for example in an infant. Such methods can include immunosuppressing the patient, for example by administration of a myeloablative regimen, administering an umbilical cord blood transplant (UCBT) (such as an allogenic UCBT), and increasing expression of galactocerebrosidase (GALC) in the patient (e.g., by using gene editing).

39 Claims, 4 Drawing Sheets

Specification includes a Sequence Listing.

(56)          References Cited

OTHER PUBLICATIONS

Escolar et al., "Transplantation of Umbilical-Cord Blood in Babies with Infantile Krabbe's Disease," *N Engl J Med.* 352:2069-2081, 2005.

Gupta et al., "Regional differences in fiber tractography predict neurodevelopmental outcomes in neonates with infantile Krabbe disease," *NeuroImage: Clinical.* 7:792-798, 2014.

Hocquemiller et al., "Adeno-Associated Virus-Based Gene Therapy for CNS Diseases," *Hum Gene Ther.* 27:478-496, 2016.

Kodama et al., "Glycosylceramide synthesis in the developing spinal cord and kidney of the twitcher mouse, an enzymatically authentic model of human Krabbe disease," *J Neurochem.* 39:1314-1318, 1982.

Meneghini et al.. , "Pervasive supply of therapeutic lysosomal enzymes in the CNS of normal and Krabbe-affected non-human primates by intracerebral lentiviral gene therapy," *EMBO Mol Med.* 8:489-510, 2016.

Morgan et al., "Hematopoietic Stem Cell Gene Therapy: Progress and Lessons Learned," *Cell Stem Cell* 21:574-590, 2017.

Prasad and Kurtzberg, "Cord blood and bone marrow transplantation in inherited metabolic diseases: scientific basis, current status and future directions," *Br J Haemotol* 148:346-372, 2009.

Rafi et al., "Long-term Improvements in Lifespan and Pathology in CNS and PNS After BMT Plus One Intravenous Injection of AAVrh10-GALC in Twitcher Mice," *Mol Ther.* 23:1681-1690, 2015.

Shim et al., "Therapeutic gene editing: delivery and regulatory perspectives," *Acta Pharm. Sinica* 38:738-753, 2017.

International Search Report and Written Opinion mailed on May 16, 2019 for International Application No. PCT/US2018/014370 (10 pages).

Chen et al., "Cloning and expression of cDNA encoding human galactocerebrosidase, the enzyme deficient in globoid cell leukodystrophy," *Human Molecular Genetics,* vol. 2, No. 11:1841-1845, 1993.

Luzi et al., "Structure and Organization of the Human Galactocerebrosidase (GALC) Gene," *GENOMICS* 26:407-409, 1995.

Tappino et al., "Identification and Characterization of 15 Novel GALC Gene Mutations Causing Krabbe Disease," *Human Mutation Mutation in Brief* 31: E1894-E1914, 2010.

GenBank Accession No. NM_000153.3, Oct. 7, 2016 (4 pages).

Deane et al., "Insights into Krabbe disease from structures of galactocerebrosidase," *Proc Natl Acad Sci USA* 108(37):15169-15173, Sep. 13, 2011.

Hill et al., "Structural snapshots illustrate the catalytic cycle of beta-galactocerebrosidase, the defective enzyme in Krabbe disease," *Proc Natl Acad Sci USA* 110(51):20479-20484, Dec. 17, 2013.

Malgieri et al., "Bone marrow and umbilical cord blood human mesenchymal stem cells: state of the art," *International Journal of Clinical and Experimental Medicine* 3.4: 248-269, 2010.

Lee et al., "Molecular characterization of mutations that cause globoid cell leukodystrophy and pharmacological rescue using small molecule chemical chaperones," *J Neurosci* 30(16):5489-5497, Apr. 21, 2010.

P54803 GALC_Human, Protein galactocerebrosidase, UniProtKB information sheet, retrieved Jan. 30, 2024, 16 pages.

"Reduced Intensity Conditioning in Patients Aged ≤35 With Non-Malignant Disorders Undergoing UCBT, BMT, or PBSCT (RIC HSCT NMD)", ClinicalTrials.gov Identifier: NCT01962415, Submitted Dec. 1, 2015, <<https://classic.clinicaltrials.gov/ct2/history/NCT01962415?V_5=View#StudyPageTop>>, retrieved Sep. 11, 2023.

Spratley et al., "Molecular Mechanisms of Disease Pathogenesis Differ in Krabbe Disease Variants," *Traffic* 17(8):908-922, Aug. 2016.

Yao et al., "Infusion of allogeneic umbilical cord blood hematopoietic stem cells in patients with chemotherapy-related myelosuppression," *Exp Ther Med* 8(6):1946-1950, 2014.

* cited by examiner

FIG. 1

A ─╫─ iv at PND10 only (n = 20)
B ─╫─ BMT only (n = 10)
C ─╫─ BMT + iv at PND 10 (n = 16)
D ─╫─ Untreated affected (n = 9)

Percent survival

Days

```
                         SEQUENCE LISTING

<160> NUMBER OF SEQ ID NOS: 6

<210> SEQ ID NO 1
<211> LENGTH: 3897
<212> TYPE: DNA
<213> ORGANISM: Homo sapiens
<220> FEATURE:
<221> NAME/KEY: CDS
<222> LOCATION: (108)..(2162)

<400> SEQUENCE: 1
actcaaaatg gcggcggcgg cgtcagcatc agcggcctcc tgcccgtatc tatcgtggcg      60
gcgacgggac ccgcctccct gggcgccgga gtcatgtgac ccacaca atg gct gag     116
                                                        Met Ala Glu
                                                        1 tgg cta ctc tcg gct tcc tgg caa cgc cga gcg aaa gct atg act gcg     164
Trp Leu Leu Ser Ala Ser Trp Gln Arg Arg Ala Lys Ala Met Thr Ala
    5                   10                  15 gcc gcg ggt tcg gcg ggc cgc gcc gcg gtg ccc ttg ctg ctg tgt gcg     212
Ala Ala Gly Ser Ala Gly Arg Ala Ala Val Pro Leu Leu Leu Cys Ala
20                  25                  30                  35 ctg ctg gcg ccc ggc ggc gcg tac gtg ctc gac gac tcc gac ggg ctg     260
Leu Leu Ala Pro Gly Gly Ala Tyr Val Leu Asp Asp Ser Asp Gly Leu
                40                  45                  50 ggc cgg gag ttc gac ggc atc ggc gcg gtc agc ggc ggc ggg gca acc     308
Gly Arg Glu Phe Asp Gly Ile Gly Ala Val Ser Gly Gly Gly Ala Thr
                55                  60                  65 tcc cga ctt cta gta aat tac cca gag ccc tat cgt tct cag ata ttg     356
Ser Arg Leu Leu Val Asn Tyr Pro Glu Pro Tyr Arg Ser Gln Ile Leu
            70                  75                  80 gat tat ctc ttt aag ccg aat ttt ggt gcc tct ttg cat att tta aaa     404
Asp Tyr Leu Phe Lys Pro Asn Phe Gly Ala Ser Leu His Ile Leu Lys
        85                  90                  95 gtg gaa ata ggt ggt gat ggg cag aca aca gac ggc act gag ccc tcc     452
Val Glu Ile Gly Gly Asp Gly Gln Thr Thr Asp Gly Thr Glu Pro Ser
100                 105                 110                 115 cac atg cat tat gca cta gat gag aat tat ttc cga gga tac gag tgg     500
His Met His Tyr Ala Leu Asp Glu Asn Tyr Phe Arg Gly Tyr Glu Trp
                120                 125                 130 tgg ttg atg aaa gaa gct aag aag agg aat ccc aat att aca ctc att     548
Trp Leu Met Lys Glu Ala Lys Lys Arg Asn Pro Asn Ile Thr Leu Ile
                135                 140                 145 ggg ttg cca tgg tca ttc cct gga tgg ctg gga aaa ggt ttc gac tgg     596
Gly Leu Pro Trp Ser Phe Pro Gly Trp Leu Gly Lys Gly Phe Asp Trp
            150                 155                 160 cct tat gtc aat ctt cag ctg act gcc tat tat gtc gtg acc tgg att     644
Pro Tyr Val Asn Leu Gln Leu Thr Ala Tyr Tyr Val Val Thr Trp Ile
        165                 170                 175 gtg ggc gcc aag cgt tac cat gat ttg gac att gat tat att gga att     692
Val Gly Ala Lys Arg Tyr His Asp Leu Asp Ile Asp Tyr Ile Gly Ile
180                 185                 190                 195 tgg aat gag agg tca tat aat gcc aat tat att aag ata tta aga aaa     740
Trp Asn Glu Arg Ser Tyr Asn Ala Asn Tyr Ile Lys Ile Leu Arg Lys
                200                 205                 210 atg ctg aat tat caa ggt ctc cag cga gtg aaa atc ata gca agt gat     788
Met Leu Asn Tyr Gln Gly Leu Gln Arg Val Lys Ile Ile Ala Ser Asp
```

-continued

```
                215                 220                 225 aat ctc tgg gag tcc atc tct gca tcc atg ctc ctt gat gcc gaa ctc      836
Asn Leu Trp Glu Ser Ile Ser Ala Ser Met Leu Leu Asp Ala Glu Leu
        230                 235                 240 ttc aag gtg gtt gat gtt ata ggg gct cat tat cct gga acc cat tca      884
Phe Lys Val Val Asp Val Ile Gly Ala His Tyr Pro Gly Thr His Ser
        245                 250                 255 gca aaa gat gca aag ttg act ggg aag aag ctt tgg tct tct gaa gac      932
Ala Lys Asp Ala Lys Leu Thr Gly Lys Lys Leu Trp Ser Ser Glu Asp
260                 265                 270                 275 ttt agc act tta aat agt gac atg ggt gca ggc tgc tgg ggt cgc att      980
Phe Ser Thr Leu Asn Ser Asp Met Gly Ala Gly Cys Trp Gly Arg Ile
                280                 285                 290 tta aat cag aat tat atc aat ggc tat atg act tcc aca atc gca tgg     1028
Leu Asn Gln Asn Tyr Ile Asn Gly Tyr Met Thr Ser Thr Ile Ala Trp
                295                 300                 305 aat tta gtg gct agt tac tat gaa cag ttg cct tat ggg aga tgc ggg     1076
Asn Leu Val Ala Ser Tyr Tyr Glu Gln Leu Pro Tyr Gly Arg Cys Gly
        310                 315                 320 ttg atg acg gcc cag gag cca tgg agt ggg cac tac gtg gta gaa tct     1124
Leu Met Thr Ala Gln Glu Pro Trp Ser Gly His Tyr Val Val Glu Ser
        325                 330                 335 cct gtc tgg gta tca gct cat acc act cag ttt act caa cct ggc tgg     1172
Pro Val Trp Val Ser Ala His Thr Thr Gln Phe Thr Gln Pro Gly Trp
340                 345                 350                 355 tat tac ctg aag aca gtt ggc cat tta gag aaa gga gga agc tac gta     1220
Tyr Tyr Leu Lys Thr Val Gly His Leu Glu Lys Gly Gly Ser Tyr Val
                360                 365                 370 gct ctg act gat ggc tta ggg aac ctc acc atc atc att gaa acc atg     1268
Ala Leu Thr Asp Gly Leu Gly Asn Leu Thr Ile Ile Ile Glu Thr Met
                375                 380                 385 agt cat aaa cat tct aag tgc ata cgg cca ttt ctt cct tat ttc aat     1316
Ser His Lys His Ser Lys Cys Ile Arg Pro Phe Leu Pro Tyr Phe Asn
        390                 395                 400 gtg tca caa caa ttt gcc acc ttt gtt ctt aag gga tct ttt agt gaa     1364
Val Ser Gln Gln Phe Ala Thr Phe Val Leu Lys Gly Ser Phe Ser Glu
        405                 410                 415 ata cca gag cta cag gta tgg tat acc aaa ctt gga aaa aca tcc gaa     1412
Ile Pro Glu Leu Gln Val Trp Tyr Thr Lys Leu Gly Lys Thr Ser Glu
420                 425                 430                 435 aga ttt ctt ttt aag cag ctg gat tct cta tgg ctc ctt gac agc gat     1460
Arg Phe Leu Phe Lys Gln Leu Asp Ser Leu Trp Leu Leu Asp Ser Asp
                440                 445                 450 ggc agt ttc aca ctg agc ctg cat gaa gat gag ctg ttc aca ctc acc     1508
Gly Ser Phe Thr Leu Ser Leu His Glu Asp Glu Leu Phe Thr Leu Thr
                455                 460                 465 act ctc acc act ggt cgc aaa ggc agc tac ccg ctt cct cca aaa tcc     1556
Thr Leu Thr Thr Gly Arg Lys Gly Ser Tyr Pro Leu Pro Pro Lys Ser
        470                 475                 480 cag ccc ttc cca agt acc tat aag gat gat ttc aat gtt gat tac cca     1604
Gln Pro Phe Pro Ser Thr Tyr Lys Asp Asp Phe Asn Val Asp Tyr Pro
        485                 490                 495 ttt ttt agt gaa gct cca aac ttt gct gat caa act ggt gta ttt gaa     1652
Phe Phe Ser Glu Ala Pro Asn Phe Ala Asp Gln Thr Gly Val Phe Glu
500                 505                 510                 515 tat ttt aca aat att gaa gac cct ggc gag cat cac ttc acg cta cgc     1700
Tyr Phe Thr Asn Ile Glu Asp Pro Gly Glu His His Phe Thr Leu Arg
                520                 525                 530 caa gtt ctc aac cag aga ccc att acg tgg gct gcc gat gca tcc aac     1748
Gln Val Leu Asn Gln Arg Pro Ile Thr Trp Ala Ala Asp Ala Ser Asn
```

-continued

```
Gln Val Leu Asn Gln Arg Pro Ile Thr Trp Ala Ala Asp Ala Ser Asn
        535             540             545 aca atc agt att ata gga gac tac aac tgg acc aat ctg act ata aag   1796
Thr Ile Ser Ile Ile Gly Asp Tyr Asn Trp Thr Asn Leu Thr Ile Lys
        550             555             560 tgt gat gta tac ata gag acc cct gac aca gga ggt gtg ttc att gca   1844
Cys Asp Val Tyr Ile Glu Thr Pro Asp Thr Gly Gly Val Phe Ile Ala
        565             570             575 gga aga gta aat aaa ggt ggt att ttg att aga agt gcc aga gga att   1892
Gly Arg Val Asn Lys Gly Gly Ile Leu Ile Arg Ser Ala Arg Gly Ile
580             585             590             595 ttc ttc tgg att ttt gca aat gga tct tac agg gtt aca ggt gat tta   1940
Phe Phe Trp Ile Phe Ala Asn Gly Ser Tyr Arg Val Thr Gly Asp Leu
                600             605             610 gct gga tgg att ata tat gct tta gga cgt gtt gaa gtt aca gca aaa   1988
Ala Gly Trp Ile Ile Tyr Ala Leu Gly Arg Val Glu Val Thr Ala Lys
            615             620             625 aaa tgg tat aca ctc acg tta act att aag ggt cat ttc acc tct ggc   2036
Lys Trp Tyr Thr Leu Thr Leu Thr Ile Lys Gly His Phe Thr Ser Gly
        630             635             640 atg ctg aat gac aag tct ctg tgg aca gac atc cct gtg aat ttt cca   2084
Met Leu Asn Asp Lys Ser Leu Trp Thr Asp Ile Pro Val Asn Phe Pro
        645             650             655 aag aat ggc tgg gct gca att gga act cac tcc ttt gaa ttt gca cag   2132
Lys Asn Gly Trp Ala Ala Ile Gly Thr His Ser Phe Glu Phe Ala Gln
660             665             670             675 ttt gac aac ttt ctt gtg gaa gcc aca cgc taatacttaa cagggcatca     2182
Phe Asp Asn Phe Leu Val Glu Ala Thr Arg
            680             685 tagaatactc tggattttct tcccttcttt ttggttttgg ttcagagcca attcttgttt   2242
cattggaaca gtatatgagg cttttgagac taaaaataat gaagagtaaa aggggagaga   2302
aatttatttt taatttaccc tgtggaagat tttattagaa ttaattccaa ggggaaaact   2362
ggtgaatctt taacattacc tggtgtgttc cctaacattc aaactgtgca ttggccatac   2422
ccttaggagt ggtttgagta gtacagacct cgaagccttg ctgctaacac tgaggtagct   2482
ctcttcatct tatttgcaag cggtcctgta gatggcagta acttgatcat cactgagatg   2542
tatttatgca tgctgaccgt gtgtccaagt gagccagtgt cttcatcaca agatgatgct   2602
gccataatag aaagctgaag aacactagaa gtagcttttt gaaaaccact tcaacctgtt   2662
atgctttatg ctctaaaaag tattttttta ttttcctttt taagatgata cttttgaaat   2722
gcaggatatg atgagtggga tgattttaaa aatgcctctt taataaacta cctctaacac   2782
tatttctgca gtaatagata ttagcagatt aattgggtta tttgcattat ttaatttttt   2842
tgattccaag ttttggtctt gtaaccacta taactctctg tgaacgtttt tccaggtggc   2902
tggaagaagg aagaaaacct gatatagcca atgctgttgt agtcgtttcc tcagcctcat   2962
ctcactgtgc tgtggtctgt cctcacatgt gcactggtaa cagactcaca cagctgatga   3022
atgcttttct ctccttatgt gtggaaggag gggagcactt agacatttgc taactcccag   3082
aattggatca tctcctaaga tgtacttact ttttaaagtc caaatatgtt tatatttaaa   3142
tatacgtgag cgtgttcatc atgttgtatg atttatacta agcattaatg tggctctatg   3202
tagcaaatca gttattcatg taggtaaagt aaatctagaa ttatttataa gaattactca   3262
ttgaactaat tctactattt aggaatttgt aagagtctaa cataggctta gctacagtga   3322
agttttgcat tgcttttgaa gacaagaaga taagtgctag aataaataag attacagaga   3382
```

-continued

```
aaatttttg ttaaaaccaa gtgatttcca gctgatgtat ctaatatttt ttaaaacgaa      3442
cattatagag gtgtaattta tttacaataa aatgttccta ctttaaatat acaattcagt      3502
gagttttgat aaattgatat acccatgtaa ccaacactcc agtcaagctt cagaatattt      3562
ccatcacccc agaaggttct cttgtatacc tgctcagtca gttcctttca ctcccaattg      3622
ttggcagcca ttgataggaa ttctatcact ataggttagt tttctttgtt ccagaacatc      3682
atgaaagcgg cgtcatgtac tgtgtattct tatgaatggt ttctttccat cagcataatg      3742
atttgagatt tgtccatgtt gtgtgattca gtggtttgtt ccttcttatt tctgaagagt      3802
tttccattgt atgaatatac cacaatttgt ttcctcccca ccagtttctg atactacaat      3862
taaaactgtc tacatttaca aaaaaaaaaa aaaaa                                 3897
```

```
<210> SEQ ID NO 2
<211> LENGTH: 685
<212> TYPE: PRT
<213> ORGANISM: Homo sapiens

<400> SEQUENCE: 2

Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
                20                  25                  30

Leu Cys Ala Leu Leu Ala Pro Gly Gly Ala Tyr Val Leu Asp Asp Ser
            35                  40                  45

Asp Gly Leu Gly Arg Glu Phe Asp Gly Ile Gly Ala Val Ser Gly Gly
        50                  55                  60

Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95

Ile Leu Lys Val Glu Ile Gly Gly Asp Gly Gln Thr Thr Asp Gly Thr
                100                 105                 110

Glu Pro Ser His Met His Tyr Ala Leu Asp Glu Asn Tyr Phe Arg Gly
            115                 120                 125

Tyr Glu Trp Trp Leu Met Lys Glu Ala Lys Lys Arg Asn Pro Asn Ile
            130                 135                 140

Thr Leu Ile Gly Leu Pro Trp Ser Phe Pro Gly Trp Leu Gly Lys Gly
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
            195                 200                 205

Leu Arg Lys Met Leu Asn Tyr Gln Gly Leu Gln Arg Val Lys Ile Ile
        210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
            275                 280                 285
```

-continued

```
Gly Arg Ile Leu Asn Gln Asn Tyr Ile Asn Gly Tyr Met Thr Ser Thr
    290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
                340                 345                 350

Pro Gly Trp Tyr Tyr Leu Lys Thr Val Gly His Leu Glu Lys Gly Gly
                355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
                420                 425                 430

Thr Ser Glu Arg Phe Leu Phe Lys Gln Leu Asp Ser Leu Trp Leu Leu
                435                 440                 445

Asp Ser Asp Gly Ser Phe Thr Leu Ser Leu His Glu Asp Glu Leu Phe
    450                 455                 460

Thr Leu Thr Thr Leu Thr Thr Gly Arg Lys Gly Ser Tyr Pro Leu Pro
465                 470                 475                 480

Pro Lys Ser Gln Pro Phe Pro Ser Thr Tyr Lys Asp Asp Phe Asn Val
                485                 490                 495

Asp Tyr Pro Phe Phe Ser Glu Ala Pro Asn Phe Ala Asp Gln Thr Gly
                500                 505                 510

Val Phe Glu Tyr Phe Thr Asn Ile Glu Asp Pro Gly Glu His His Phe
                515                 520                 525

Thr Leu Arg Gln Val Leu Asn Gln Arg Pro Ile Thr Trp Ala Ala Asp
    530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
                565                 570                 575

Phe Ile Ala Gly Arg Val Asn Lys Gly Gly Ile Leu Ile Arg Ser Ala
                580                 585                 590

Arg Gly Ile Phe Phe Trp Ile Phe Ala Asn Gly Ser Tyr Arg Val Thr
                595                 600                 605

Gly Asp Leu Ala Gly Trp Ile Ile Tyr Ala Leu Gly Arg Val Glu Val
    610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
                645                 650                 655

Asn Phe Pro Lys Asn Gly Trp Ala Ala Ile Gly Thr His Ser Phe Glu
                660                 665                 670

Phe Ala Gln Phe Asp Asn Phe Leu Val Glu Ala Thr Arg
                675                 680                 685
```

<210> SEQ ID NO 3
<211> LENGTH: 2217

```
<212> TYPE: DNA
<213> ORGANISM: Artificial Sequence
<220> FEATURE:
<223> OTHER INFORMATION: AAV serotype rh.10 capsid
<220> FEATURE:
<221> NAME/KEY: CDS
<222> LOCATION: (1)..(2217)

<400> SEQUENCE: 3 atg gct gcc gat ggt tat ctt cca gat tgg ctc gag gac aac ctc tct        48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aaa ccc        96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct       144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc       192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac       240
Val Asn Ala Ala Asp Ala Ala Ala Leu Glu His Asp Lys Ala Tyr Asp
65                  70                  75                  80 cag cag ctc aaa gcg ggt gac aat ccg tac ctg cgg tat aac cac gcc       288
Gln Gln Leu Lys Ala Gly Asp Asn Pro Tyr Leu Arg Tyr Asn His Ala
                85                  90                  95 gac gcc gag ttt cag gag cgt ctg caa gaa gat acg tct ttt ggg ggc       336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct       384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga       432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc       480
Pro Val Glu Pro Ser Pro Gln Arg Ser Pro Asp Ser Ser Thr Gly Ile
145                 150                 155                 160 ggc aag aaa ggc cag cag ccc gcg aaa aag aga ctc aac ttt ggg cag       528
Gly Lys Lys Gly Gln Gln Pro Ala Lys Lys Arg Leu Asn Phe Gly Gln
                165                 170                 175 act ggc gac tca gag tca gtg ccc gac cct caa cca atc gga gaa ccc       576
Thr Gly Asp Ser Glu Ser Val Pro Asp Pro Gln Pro Ile Gly Glu Pro
            180                 185                 190 ccc gca ggc ccc tct ggt ctg gga tct ggt aca atg gct gca ggc ggt       624
Pro Ala Gly Pro Ser Gly Leu Gly Ser Gly Thr Met Ala Ala Gly Gly
        195                 200                 205 ggc gct cca atg gca gac aat aac gaa ggc gcc gac gga gtg ggt agt       672
Gly Ala Pro Met Ala Asp Asn Asn Glu Gly Ala Asp Gly Val Gly Ser
    210                 215                 220 tcc tca gga aat tgg cat tgc gat tcc aca tgg ctg ggc gac aga gtc       720
Ser Ser Gly Asn Trp His Cys Asp Ser Thr Trp Leu Gly Asp Arg Val
225                 230                 235                 240 atc acc acc agc acc cga acc tgg gcc ctc ccc acc tac aac aac cac       768
Ile Thr Thr Ser Thr Arg Thr Trp Ala Leu Pro Thr Tyr Asn Asn His
                245                 250                 255 ctc tac aag caa atc tcc aac ggg act tcg gga gga agc acc aac gac       816
Leu Tyr Lys Gln Ile Ser Asn Gly Thr Ser Gly Gly Ser Thr Asn Asp
            260                 265                 270 aac acc tac ttc ggc tac agc acc ccc tgg ggg tat ttt gac ttt aac       864
```

-continued

```
Asn Thr Tyr Phe Gly Tyr Ser Thr Pro Trp Gly Tyr Phe Asp Phe Asn
    275                 280             285 aga ttc cac tgc cac ttc tca cca cgt gac tgg cag cga ctc atc aac      912
Arg Phe His Cys His Phe Ser Pro Arg Asp Trp Gln Arg Leu Ile Asn
    290                 295             300 aac aac tgg gga ttc cgg ccc aag aga ctc aac ttc aag ctc ttc aac      960
Asn Asn Trp Gly Phe Arg Pro Lys Arg Leu Asn Phe Lys Leu Phe Asn
305             310             315                 320 atc cag gtc aag gag gtc acg cag aat gaa ggc acc aag acc atc gcc     1008
Ile Gln Val Lys Glu Val Thr Gln Asn Glu Gly Thr Lys Thr Ile Ala
                325             330             335 aat aac ctt acc agc acg att cag gtc ttt acg gac tcg gaa tac cag     1056
Asn Asn Leu Thr Ser Thr Ile Gln Val Phe Thr Asp Ser Glu Tyr Gln
            340             345             350 ctc ccg tac gtc ctc ggc tct gcg cac cag ggc tgc ctg cct ccg ttc     1104
Leu Pro Tyr Val Leu Gly Ser Ala His Gln Gly Cys Leu Pro Pro Phe
            355             360             365 ccg gcg gac gtc ttc atg att cct cag tac ggg tac ctg act ctg aac     1152
Pro Ala Asp Val Phe Met Ile Pro Gln Tyr Gly Tyr Leu Thr Leu Asn
    370             375             380 aat ggc agt cag gcc gtg ggc cgt tcc tcc ttc tac tgc ctg gag tac     1200
Asn Gly Ser Gln Ala Val Gly Arg Ser Ser Phe Tyr Cys Leu Glu Tyr
385             390             395                 400 ttt cct tct caa atg ctg aga acg ggc aac aac ttt gag ttc agc tac     1248
Phe Pro Ser Gln Met Leu Arg Thr Gly Asn Asn Phe Glu Phe Ser Tyr
                405             410             415 cag ttt gag gac gtg cct ttt cac agc agc tac gcg cac agc caa agc     1296
Gln Phe Glu Asp Val Pro Phe His Ser Ser Tyr Ala His Ser Gln Ser
            420             425             430 ctg gac cgg ctg atg aac ccc ctc atc gac cag tac ctg tac tac ctg     1344
Leu Asp Arg Leu Met Asn Pro Leu Ile Asp Gln Tyr Leu Tyr Tyr Leu
            435             440             445 tct cgg act cag tcc acg gga ggt acc gca gga act cag cag ttg cta     1392
Ser Arg Thr Gln Ser Thr Gly Gly Thr Ala Gly Thr Gln Gln Leu Leu
    450             455             460 ttt tct cag gcc ggg cct aat aac atg tcg gct cag gcc aaa aac tgg     1440
Phe Ser Gln Ala Gly Pro Asn Asn Met Ser Ala Gln Ala Lys Asn Trp
465             470             475                 480 cta ccc ggg ccc tgc tac cgg cag caa cgc gtc tcc acg aca ctg tcg     1488
Leu Pro Gly Pro Cys Tyr Arg Gln Gln Arg Val Ser Thr Thr Leu Ser
            485             490             495 caa aat aac aac agc aac ttt gcc tgg acc ggt gcc acc aag tat cat     1536
Gln Asn Asn Asn Ser Asn Phe Ala Trp Thr Gly Ala Thr Lys Tyr His
            500             505             510 ctg aat ggc aga gac tct ctg gta aat ccc ggt gtc gct atg gca acc     1584
Leu Asn Gly Arg Asp Ser Leu Val Asn Pro Gly Val Ala Met Ala Thr
            515             520             525 cac aag gac gac gaa gag cga ttt ttt ccg tcc agc gga gtc tta atg     1632
His Lys Asp Asp Glu Glu Arg Phe Phe Pro Ser Ser Gly Val Leu Met
    530             535             540 ttt ggg aaa cag gga gct gga aaa gac aac gtg gac tat agc agc gtt     1680
Phe Gly Lys Gln Gly Ala Gly Lys Asp Asn Val Asp Tyr Ser Ser Val
545             550             555                 560 atg cta acc agt gag gaa gaa att aaa acc acc aac cca gtg gcc aca     1728
Met Leu Thr Ser Glu Glu Glu Ile Lys Thr Thr Asn Pro Val Ala Thr
                565             570             575 gaa cag tac ggc gtg gtg gcc gat aac ctg caa cag caa aac gcc gct     1776
Glu Gln Tyr Gly Val Val Ala Asp Asn Leu Gln Gln Gln Asn Ala Ala
            580             585             590
```

-continued

```
cct att gta ggg gcc gtc aac agt caa gga gcc tta cct ggc atg gtc      1824
Pro Ile Val Gly Ala Val Asn Ser Gln Gly Ala Leu Pro Gly Met Val
        595                 600                 605 tgg cag aac cgg gac gtg tac ctg cag ggt cct atc tgg gcc aag att      1872
Trp Gln Asn Arg Asp Val Tyr Leu Gln Gly Pro Ile Trp Ala Lys Ile
    610                 615                 620 cct cac acg gac gga aac ttt cat ccc tcg ccg ctg atg gga ggc ttt      1920
Pro His Thr Asp Gly Asn Phe His Pro Ser Pro Leu Met Gly Gly Phe
625                 630                 635                 640 gga ctg aaa cac ccg cct cct cag atc ctg att aag aat aca cct gtt      1968
Gly Leu Lys His Pro Pro Pro Gln Ile Leu Ile Lys Asn Thr Pro Val
                645                 650                 655 ccc gcg gat cct cca act acc ttc agt caa gct aag ctg gcg tcg ttc      2016
Pro Ala Asp Pro Pro Thr Thr Phe Ser Gln Ala Lys Leu Ala Ser Phe
                660                 665                 670 atc acg cag tac agc acc gga cag gtc agc gtg gaa att gaa tgg gag      2064
Ile Thr Gln Tyr Ser Thr Gly Gln Val Ser Val Glu Ile Glu Trp Glu
        675                 680                 685 ctg cag aaa gaa aac agc aaa cgc tgg aac cca gag att caa tac act      2112
Leu Gln Lys Glu Asn Ser Lys Arg Trp Asn Pro Glu Ile Gln Tyr Thr
    690                 695                 700 tcc aac tac tac aaa tct aca aat gtg gac ttt gct gtt aac aca gat      2160
Ser Asn Tyr Tyr Lys Ser Thr Asn Val Asp Phe Ala Val Asn Thr Asp
705                 710                 715                 720 ggc act tat tct gag cct cgc ccc atc ggc acc cgt tac ctc acc cgt      2208
Gly Thr Tyr Ser Glu Pro Arg Pro Ile Gly Thr Arg Tyr Leu Thr Arg
                725                 730                 735 aat ctg taa                                                            2217
Asn Leu
```

```
<210> SEQ ID NO 4
<211> LENGTH: 738
<212> TYPE: PRT
<213> ORGANISM: Artificial Sequence
<220> FEATURE:
<223> OTHER INFORMATION: Synthetic Construct

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
```

-continued

```
                580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
    675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

<210> SEQ ID NO 5
<211> LENGTH: 3749
<212> TYPE: DNA
<213> ORGANISM: Homo sapiens

<400> SEQUENCE: 5

```
aaaagctatg actgcggccg cgggttcggc gggccgcgcc gcggtgccct tgctgctgtg      60
tgcgctgctg gcgcccggcg gcgcgtacgt gctcgacgac tccgacgggc tgggccggga     120
gttcgacggc atcggcgcgg tcagcggcgc ggggcaacc tcccgacttc tagtaaatta      180
cccagagccc tatcgttctc agatattgga ttatctcttt aagccgaatt ttggtgcctc     240
tttgcatatt ttaaaagtgg aaataggtgg tgatgggcag acaacagatg cactgagcc      300 ctcccacatg cattatgcac tagatgagaa ttatttccga ggatacgagt ggtggttgat     360
gaaagaagct aagaagagga atcccaatat tacactcatt gggttgccat ggtcattccc     420
tggatggctg ggaaaaggtt tcgactggcc ttatgtcaat cttcagctga ctgcctatta     480
tgtcgtgacc tggattgtgg gcgccaagcg ttaccatgat ttggacattg attatattgg     540
aatttggaat gagaggtcat ataatgccaa ttatattaag atattaagaa aaatgctgaa     600
ttatcaaggt ctccagcgag tgaaaatcat agcaagtgat aatctctggg agtccatctc     660
tgcatccatg ctccttgatg ccgaactctt caaggtggtt gatgttatag gggctcatta     720
tcctggaacc cattcagcaa aagatgcaaa gttgactggg aagaagcttt ggtcttctga     780
agactttagc actttaaata gtgacatggg tgcaggctgc tggggtcgca ttttaaatca     840
gaattatatc aatggctata tgacttccac aatcgcatgg aatttagtgg ctagttacta     900
tgaacagttg ccttatggga gatgcgggtt gatgacggcc caggagccat ggagtgggca     960
ctacgtggta gaatctcctg tctgggtatc agctcatacc actcagttta ctcaacctgg    1020
ctggtattac ctgaagacag ttggccattt agagaaagga ggaagctacg tagctctgac    1080
tgatggctta gggaacctca ccatcatcat tgaaaccatg agtcataaac attctaagtg    1140
catacggcca tttcttcctt atttcaatgt gtcacaacaa tttgccacct ttgttcttaa    1200
```

-continued

```
gggatctttt agtgaaatac cagagctaca ggtatggtat accaaacttg gaaaaacatc    1260
cgaaagattt cttttaagc agctggattc tctatggctc cttgacagcg atggcagttt      1320
cacactgagc ctgcatgaag atgagctgtt cacactcacc actctcacca ctggtcgcaa    1380
aggcagctac ccgcttcctc caaaatccca gcccttccca agtacctata aggatgattt     1440
caatgttgat tacccatttt ttagtgaagc tccaaacttt gctgatcaaa ctggtgtatt    1500
tgaatatttt acaaatattg aagaccctgg cgagcatcac ttcacgctac gccaagttct    1560
caaccagaga cccattacgt gggctgccga tgcatccaac acaatcagta ttataggaga     1620
ctacaactgg accaatctga ctacaaagtg tgatgtttac atagagaccc ctgacacagg    1680
aggtgtgttc attgcaggaa gagtaaataa aggtggtatt ttgattagaa gtgccagagg    1740 aatttttcttc tggattttttg caaatggatc ttacagggtt acaggtgatt tagctggatg    1800
gattatatat gctttaggac gtgttgaagt tacagcaaaa aaatggtata cactcacgtt    1860
aactattaag ggtcatttcg cctctggcat gctgaatgac aagtctctgt ggacagacat    1920
ccctgtgaat tttccaaaga atggctgggc tgcaattgga actcactcct ttgaatttgc    1980
acagtttgac aactttcttg tggaagccac acgctaatac ttaacagggc atcatagaat    2040
actctggatt ttcttcccctt cttttttggtt ttggttcaga gccaattctt gtttcattgg    2100
aacagtatat gaggcttttg agactaaaaa taatgaagag taaaaggggga gagaaattta   2160 tttttaattt accctgtgga agattttatt agaattaatt ccaaggggaa aactggtgaa    2220
tctttaacat tacctggtgt gttccctaac attcaaactg tgcattggcc ataccctttag    2280 gagtggtttg agtagtacag acctcgaagc cttgctgcta acactgaggt agctctcttc    2340
atcttatttg caagcggtcc tgtagatggc agtaacttga tcatcactga gatgtattta    2400
tgcatgctga ccgtgtgtcc aagtgagcca gtgtcttcat cacaagatga tgctgccata    2460
atagaaagct gaagaacact agaagtagct ttttgaaaac cacttcaacc tgttatgctt     2520
tatgctctaa aaagtatttt ttttattttc ctttttaaga tgatactttt gaaatgcagg    2580
atatgatgag tgggatgatt ttaaaaatgc ctctttaata aactacctct aacactattt    2640
ctgtggtaat agatattagc agattaattg ggttatttgc attatttaat tttttttgatt    2700 ccaagttttg gtcttgtaac cactataact ctctgtgaac atttttccag gtggctggaa    2760
gaaggaagaa aacctgatat agccaatgct gttgtagtcg tttcctcagc ctcatctcac    2820
tgtgctgtgg tctgtcctca catgtgcact ggtaacagac tcacacagct gatgaatgct    2880
tttctctcct tatgtgtgga aggaggggag cacttagaca tttgctaact cccagaattg    2940
gatcatctcc taagatgtac ttactttttta aagtccaaat atgtttatat ttaaatatac    3000
gtgagcatgt tcatcatgtt gtatgattta tactaagcat taatgtggct ctatgtagca    3060
aatcagttat tcatgtaggt aaagtaaatc tagaattatt tataagaatt actcattgaa    3120
ctaattctac tatttaggaa tttgtaagag tctaacatag gcttagctac agtgaagttt    3180
tgcattgctt ttgaagacaa gaagataagt gctagaataa ataagattac agagaaaatt    3240
ttttgttaaa accaagtgat ttccagctga tgtatctaat attttttaaa acgaacatta    3300
tagaggtgta atttatttac aataaaatgt tcctacttta aatatacaat tcagtgagtt    3360
ttgataaatt gatatacca tgtaaccaac actccagtca agcttcagaa tatttccatc     3420
accccagaag gttctcttgt atacctgctc agtcagttcc tttcactccc gattgttggc    3480
agccattgat aggaattcta tcactatagg ttagttttct ttgttccaga acatcatgaa    3540
agcggcgtca tgtactgtgt attcttatga atggtttctt tccatcagca taatgatttg    3600
```

```
agatttgtcc atgttgtgtg attcagtggt ttgttccttc ttatttctga agagttttcc     3660
attgtatgaa tataccacaa tttgtttcct ccccaccagt ttctgatact acaattaaaa     3720
ctgtctacat ttacaaaaaa aaaaaaaaaa                                       3749
```

<210> SEQ ID NO 6
<211> LENGTH: 669
<212> TYPE: PRT
<213> ORGANISM: Homo sapiens

<400> SEQUENCE: 6

```
Met Thr Ala Ala Ala Gly Ser Ala Gly Arg Ala Ala Val Pro Leu Leu
1               5                   10                  15

Leu Cys Ala Leu Leu Ala Pro Gly Gly Ala Tyr Val Leu Asp Asp Ser
                20                  25                  30

Asp Gly Leu Gly Arg Glu Phe Asp Gly Ile Gly Ala Val Ser Gly Gly
            35                  40                  45

Gly Ala Thr Ser Arg Leu Leu Val Asn Tyr Pro Glu Pro Tyr Arg Ser
        50                  55                  60

Gln Ile Leu Asp Tyr Leu Phe Lys Pro Asn Phe Gly Ala Ser Leu His
65                  70                  75                  80

Ile Leu Lys Val Glu Ile Gly Gly Asp Gly Gln Thr Thr Asp Gly Thr
                85                  90                  95

Glu Pro Ser His Met His Tyr Ala Leu Asp Glu Asn Tyr Phe Arg Gly
            100                 105                 110

Tyr Glu Trp Trp Leu Met Lys Glu Ala Lys Lys Arg Asn Pro Asn Ile
        115                 120                 125

Thr Leu Ile Gly Leu Pro Trp Ser Phe Pro Gly Trp Leu Gly Lys Gly
        130                 135                 140

Phe Asp Trp Pro Tyr Val Asn Leu Gln Leu Thr Ala Tyr Tyr Val Val
145                 150                 155                 160

Thr Trp Ile Val Gly Ala Lys Arg Tyr His Asp Leu Asp Ile Asp Tyr
                165                 170                 175

Ile Gly Ile Trp Asn Glu Arg Ser Tyr Asn Ala Asn Tyr Ile Lys Ile
            180                 185                 190

Leu Arg Lys Met Leu Asn Tyr Gln Gly Leu Gln Arg Val Lys Ile Ile
        195                 200                 205

Ala Ser Asp Asn Leu Trp Glu Ser Ile Ser Ala Ser Met Leu Leu Asp
        210                 215                 220

Ala Glu Leu Phe Lys Val Val Asp Val Ile Gly Ala His Tyr Pro Gly
225                 230                 235                 240

Thr His Ser Ala Lys Asp Ala Lys Leu Thr Gly Lys Lys Leu Trp Ser
                245                 250                 255

Ser Glu Asp Phe Ser Thr Leu Asn Ser Asp Met Gly Ala Gly Cys Trp
            260                 265                 270

Gly Arg Ile Leu Asn Gln Asn Tyr Ile Asn Gly Tyr Met Thr Ser Thr
        275                 280                 285

Ile Ala Trp Asn Leu Val Ala Ser Tyr Tyr Glu Gln Leu Pro Tyr Gly
        290                 295                 300

Arg Cys Gly Leu Met Thr Ala Gln Glu Pro Trp Ser Gly His Tyr Val
305                 310                 315                 320

Val Glu Ser Pro Val Trp Val Ser Ala His Thr Thr Gln Phe Thr Gln
                325                 330                 335

Pro Gly Trp Tyr Tyr Leu Lys Thr Val Gly His Leu Glu Lys Gly Gly
```

-continued

```
                340                345                350
Ser Tyr Val Ala Leu Thr Asp Gly Leu Gly Asn Leu Thr Ile Ile Ile
        355                360                365

Glu Thr Met Ser His Lys His Ser Lys Cys Ile Arg Pro Phe Leu Pro
        370                375                380

Tyr Phe Asn Val Ser Gln Gln Phe Ala Thr Phe Val Leu Lys Gly Ser
385                390                395                400

Phe Ser Glu Ile Pro Glu Leu Gln Val Trp Tyr Thr Lys Leu Gly Lys
                405                410                415

Thr Ser Glu Arg Phe Leu Phe Lys Gln Leu Asp Ser Leu Trp Leu Leu
                420                425                430

Asp Ser Asp Gly Ser Phe Thr Leu Ser Leu His Glu Asp Glu Leu Phe
        435                440                445

Thr Leu Thr Thr Leu Thr Thr Gly Arg Lys Gly Ser Tyr Pro Leu Pro
        450                455                460

Pro Lys Ser Gln Pro Phe Pro Ser Thr Tyr Lys Asp Asp Phe Asn Val
465                470                475                480

Asp Tyr Pro Phe Phe Ser Glu Ala Pro Asn Phe Ala Asp Gln Thr Gly
                485                490                495

Val Phe Glu Tyr Phe Thr Asn Ile Glu Asp Pro Gly Glu His His Phe
                500                505                510

Thr Leu Arg Gln Val Leu Asn Gln Arg Pro Ile Thr Trp Ala Ala Asp
        515                520                525

Ala Ser Asn Thr Ile Ser Ile Ile Gly Asp Tyr Asn Trp Thr Asn Leu
        530                535                540

Thr Thr Lys Cys Asp Val Tyr Ile Glu Thr Pro Asp Thr Gly Gly Val
545                550                555                560

Phe Ile Ala Gly Arg Val Asn Lys Gly Gly Ile Leu Ile Arg Ser Ala
                565                570                575

Arg Gly Ile Phe Phe Trp Ile Phe Ala Asn Gly Ser Tyr Arg Val Thr
                580                585                590

Gly Asp Leu Ala Gly Trp Ile Ile Tyr Ala Leu Gly Arg Val Glu Val
        595                600                605

Thr Ala Lys Lys Trp Tyr Thr Leu Thr Leu Thr Ile Lys Gly His Phe
        610                615                620

Ala Ser Gly Met Leu Asn Asp Lys Ser Leu Trp Thr Asp Ile Pro Val
625                630                635                640

Asn Phe Pro Lys Asn Gly Trp Ala Ala Ile Gly Thr His Ser Phe Glu
                645                650                655

Phe Ala Gln Phe Asp Asn Phe Leu Val Glu Ala Thr Arg
                660                665
```

TREATMENT OF KRABBE DISEASE WITH UMBILICAL CORD BLOOD TRANSPLANTION (UCBT) AND INCREASED GALACTOCEREBROSIDASE (GALC) EXPRESSION

CROSS REFERENCE TO RELATED APPLICATIONS

This application is the U.S. National Stage of International Application No. PCT/US2018/014370, filed Jan. 19, 2018, which in turn claims the benefit of U.S. Provisional Application No. 62/448,433, filed Jan. 20, 2017, which are herein incorporated by reference in their entireties.

INCORPORATION OF SEQUENCE LISTING

The Sequence Listing is submitted as an ASCI text file in the form of the file named "sequence listing.txt" (~45,800 bytes), which was created on Apr. 29, 2023, and which is incorporated by reference herein.

FIELD

This application provides methods of treating Krabbe disease by immunosuppressing the patient, providing an umbilical cord blood transplant (UCBT), and increasing expression of galactocerebrosidase (GALC) in the patient (e.g., by using a viral vector to express GALC). Also provided are similar methods for treating other genetic diseases.

BACKGROUND

Krabbe disease is a rare inherited lysosomal storage disorder caused by a deficiency or absence of galactocerebrosidase (GALC), an enzyme that is essential for the development and maintenance of normal myelination in the nervous system. Children with the most severe form of this condition, known as early infantile Krabbe disease, develop symptoms by 6 months of age and experience rapidly progressive neurodegeneration, typically leading to death by two years of age. Significant disability and premature death may also occur in patients with the later-onset forms of this disease, including the late infantile and juvenile presentations.

Treatment with umbilical cord blood transplantation (UCBT) can be effective in preserving cognition and extending lifespan in individuals with the early infantile and late infantile forms of Krabbe disease. Although UCBT halts the progression of brain degeneration prior to the onset of neurological symptoms, it is not effective in treating signs of peripheral nerve disease that result in significant motor disability for affected patients.

SUMMARY

Provided herein are novel methods for treating Krabbe disease. In some examples, such methods include immunosuppressing the subject, administering a therapeutically effective amount of umbilical cord blood to the subject (e.g., performing an UCBT), and administering a therapeutically effective amount of a nucleic acid molecule encoding galactocerebrosidase (GALC) to the subject (e.g., to increase GALC expression). The treated subject can have any form of Krabbe disease, such as early infantile Krabbe disease, late infantile Krabbe disease, or juvenile Krabbe disease. In some examples, the subject has early infantile Krabbe disease, and is a human infant less than 6 months of age. In some examples, the subject is a mammal, such as a human, cat, or dog.

In some examples, the umbilical cord blood is administered prior to the nucleic acid molecule encoding GALC, such as at least 12 hours, at least 24 hours, at least 48 hours, at least 72 hours, or at least 96 hours prior to the nucleic acid molecule encoding GALC. In some examples, the umbilical cord blood is allogenic to the subject. In such examples, the HLA-matched donor matches at least 4 of 6 HLA markers to the treated subject. In some examples, a total nucleated cell dose of at least $3\times10^7$/kg adjusted ideal body weight (AIBW) is administered to the subject.

The nucleic acid encoding GALC can be matched to the subject treated. Thus, for example, if the subject to be treated is a cat, a cat GALC coding sequence can be used, and if the subject to be treated is a human, a human GALC coding sequence can be used. In some examples, the nucleic acid molecule encoding GALC has at least 80%, at least 85%, at least 90%, at least 95%, at least 98%, at least 99%, or 100% sequence identity to SEQ ID NO: 1. In some examples, the nucleic acid molecule encodes a GALC protein comprising at least 80%, at least 85%, at least 90%, at least 95%, at least 98%, at least 99%, or 100% sequence identity to SEQ ID NO: 2. The nucleic acid molecule encoding GALC can be operably linked to a promoter. The nucleic acid molecule encoding GALC can be administered directly, e.g., as naked DNA, or can be administered as part of a vector, such as a plasmid or viral vector, for example one that can cross the blood-brain barrier, such as an adeno-associated vector (AAV), for example AAV serotype rh.10. In some examples, the nucleic acid molecule encoding GALC is administered intravenously. In some examples, the nucleic acid molecule encoding GALC when part of a viral vector is administered at a dose of at least $2\times10^{14}$ gc per subject. In some examples, the nucleic acid molecule encoding GALC when part of a viral vector is administered at a dose of at least $1\times10^{11}$ gc/kg, at least $1\times10^{12}$ gc/kg, at least $1\times10^{13}$ gc/kg or at least $1\times10^{14}$ gc/kg.

The subject can be immunosuppressed prior to receiving the UBCT and the nucleic acid molecule encoding GALC. In some examples, such a step includes administering a therapeutically effective amount of alemtuzumab, hydroxyurea, fludarabine, and busulfan. In some examples, such a step includes administration of reagents to decrease GVHD, such as a therapeutically effective amount of tacrolimus and mycophenolate mofetil (MMF).

In addition to methods for treating Krabbe disease, the disclosure provides methods for treating a genetic disease in a subject, such as a mammalian subject. The methods reduce an undesired immune response (e.g., antibody production) against reagents used in gene therapy (e.g., viral vector protein or a new protein not previously produced by the subject until administration of the gene therapy). Any genetic disorder can be treated with such methods. In some examples the gene therapy increases expression of a protein, decreases expression of a protein, corrects a genome sequence error, or combinations thereof. Such methods can include ablating bone marrow in the subject (for example using chemotherapy, radiation, or both), and subsequently administering a therapeutically effective amount of hematopoietic stem cells (HSCs) to the subject to provide the subject with a new immune system. In some examples, the subject is administered a therapeutically effective amount of an immunosuppressive agent following administration of the HSCs. Following administration of the HSCs (which can be before recovery of the subject's immune system), the method includes administering a therapeutically effective amount of a therapeutic nucleic acid molecule to the subject, wherein the nucleic acid molecule corrects the genetic disease (e.g., by expressing a missing protein).

The foregoing and other objects and features of the disclosure will become more apparent from the following detailed description, which proceeds with reference to the accompanying figures.

BRIEF DESCRIPTION OF THE DRAWINGS

FIG. 1. Genome structure of AAVrh.10 expressing human GALC (hGALC). The vector designated AAVrh.10-hGALC contains the AAV2 inverted terminal repeats (ITRs), the CAG promoter, full-length human GALC cDNA, and the rabbit β-globin polyA. The CAG promoter is composed of the human cytomegalovirus (CMV) enhancer, chicken β-actin promoter and splice donor, and rabbit β-globin splice acceptor. The AAV2 based genome is pseudotyped with the AAVrh.10 capsid. One skilled in the art will appreciate that the full-length human GALC cDNA can be replaced with a full-length GALC cDNA from any mammal, such as dog, cat, mouse, rat, or dolphin.

SEQUENCE LISTING

Figure 2:
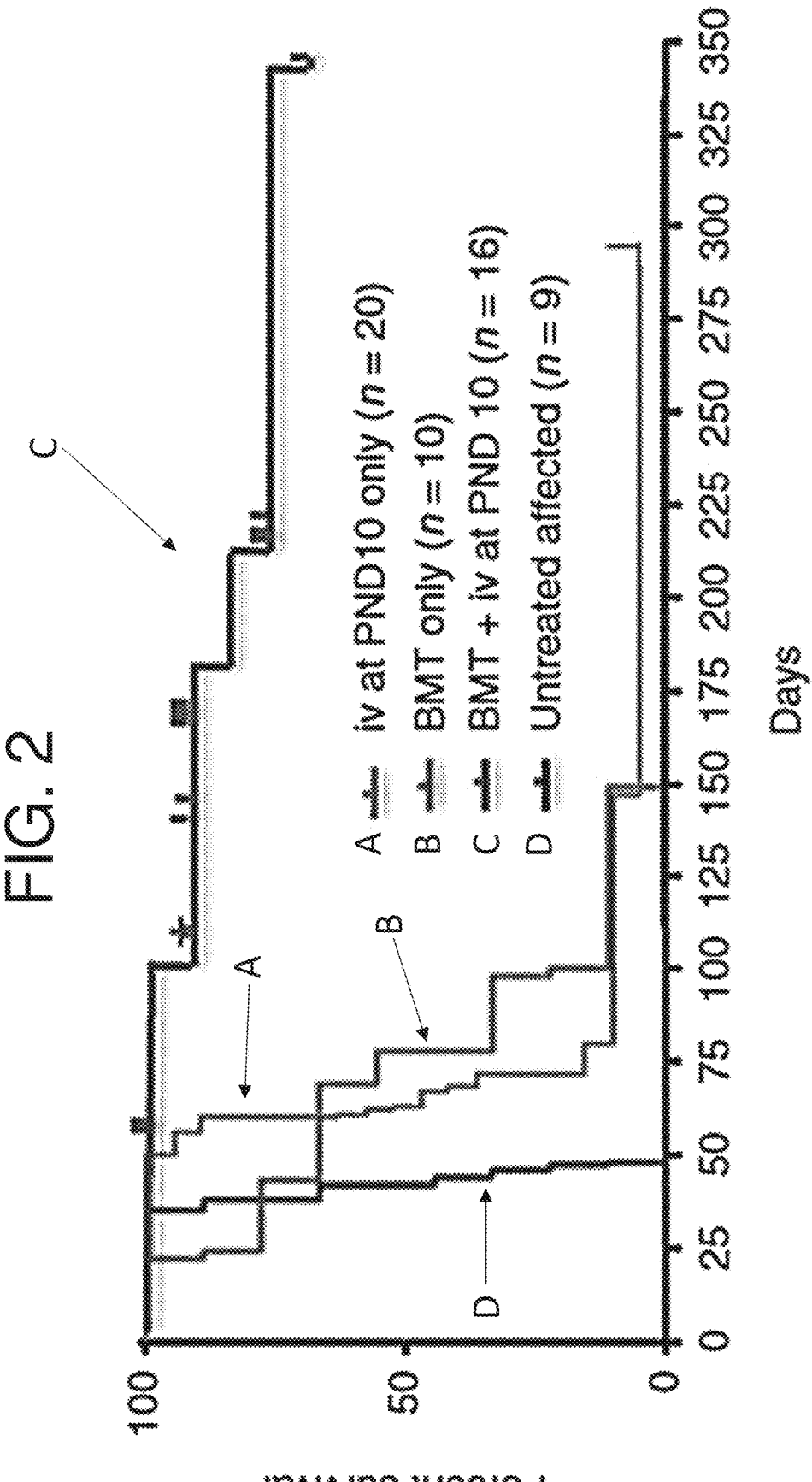
FIG. 2. Survival of twitcher mice treated with BMT and intravenous AAVrh.10-mGALC. Survival of mice treated with AAVrh.10-mGALC at PND10, BMT at PND10 (busulfan ablation), or AAVrh.10-mGALC at PND10-12 immediately following BMT (busulfan ablation). Vertical blue and green upticks represent mice still living, red upticks refer to mice sacrificed for analysis. The asterisk indicates a mouse that died from gastrointestinal complications. Note that the average survival age of mice treated with AAVrh.10-mGALC alone was about 70-75 days, although one lived much longer. From Rafi et al., *Mol. Ther.* 23:1681-90, 2015.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOS: 1 and 2 are exemplary human GALC nucleic acid and protein sequences, respectively (Gen-Bank® Accession Nos. NM_000153.3 and NP_000144.2 respectively).

SEQ ID NOS: 3 and 4 are exemplary nucleic acid and protein sequences of the capsid of AAVrh.10 (from GenBank Accession Nos. AY243015.1 and AAO88201.1).

SEQ ID NOS: 5 and 6 are exemplary human GALC nucleic acid and protein sequences, respectively (Gen-Bank® Accession Nos. BC036518.2 and AAH36518.1 respectively).

DETAILED DESCRIPTION

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers listed (as of Jan. 20, 2017) are herein incorporated by reference in their entirety.

In order to facilitate review of the various embodiments of the disclosure, the following explanations of specific terms are provided:

Administration: To provide or give a subject an agent, such as an immunosuppressive agent, umbilical cord blood, HSCs, nucleic acid molecule encoding GALC or other therapeutic nucleic acid molecule, or other therapeutic agent, by any effective route. Exemplary routes of administration include, but are not limited to, injection (such as subcutaneous, intramuscular, intradermal, intraperitoneal, intrathecal, intraosseous, and intravenous), transdermal, intranasal, and inhalation routes.

Contact: Placement in direct physical association, including a solid or a liquid form. Contacting can occur in vitro or ex vivo, for example, by adding a reagent to a sample (such as one containing umbilical cord blood), or in vivo by administering to a subject.

Effective amount: The amount of an agent (such as an immunosuppressive agent, umbilical cord blood, HSCs, nucleic acid molecule encoding GALC or other therapeutic nucleic acid molecule) that is sufficient to effect beneficial or desired results.

A effective amount (also referred to as a therapeutically effective amount) may vary depending upon one or more of: the subject and disease condition being treated, the weight and age of the subject, the severity of the disease condition, the manner of administration and the like, which can readily be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" of one or more immunosuppressive agents is an amount sufficient to achieve myelosuppression, such as reducing white blood cells by at least 99% (as compared to no administration of the immunosuppressive agent(s)). In one embodiment, an "effective amount" of umbilical cord blood is at least $3\times10^7$ total nucleated cell (TNC)/kg (30 million/kg) recipient weight, such as at least 50 million/kg, or at least 100 million/kg, to achieve engraftment at a median of Day +14-15 after RIC UCBT. In one embodiment, an "effective amount" of nucleic acid molecule encoding GALC (e.g., a vector encoding GALC) is an amount sufficient to increase the activity and/or expression of GALC in a T cell, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the nucleic acid molecule encoding GALC).

In one embodiment, an "effective amount" of immunosuppressive agent(s), umbilical cord blood, and nucleic acid molecule encoding GALC (e.g., a vector encoding GALC) are amount sufficient to increase the survival time of a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase the survival time of a treated Krabbe patient, for example by at least 6 months, at least 9 months, at least 1 year, at least 1.5 years, at least 2 years, at least 2.5 years, at least 3 years, at least 4 years, at least 5 years, at least 10 years, at least 12 years, at least 15 years, or at least 20 years (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase myelination of cells of the CNS and/or PNS of a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to reduce macrophage infiltration, astrogliosis, and/or CD68 staining in the CNS and/or PNS of a treated Krabbe patient, for example by at least 10%, at least 20%, at least 25%, at least 50%, at least 70%, at least 75%, at least 80%, at least 90%, or at least 95% (as compared to no administration of the immunosuppressive agent(s), umbilical cord blood and the nucleic acid molecule encoding GALC. In one embodiment, an "effective amount" of immunosuppressive agent(s), umbilical cord blood, and nucleic acid molecule encoding GALC (e.g., a vector encoding GALC) are amount sufficient to reduce tremors in a treated Krabbe patient, for example by at least 10%, at least 20%, at least 25%, at least 50%, at least 70%, at least 75%, at least 80%, at least 90%, or at least 95% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC) (e.g., a vector encoding GALC) are amount sufficient to increase the body weight of a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase or improve neurodevelopmental function in a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase or improve early learning (e.g., as evaluated by the Bayley Scales of Infant Development or the Mullen Scales (Mullen, E. M. (1995). *Mullen Scales of Early Learning* (AGS ed. Circle Pines, MN: American Guidance Service Inc.)) in a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase or improve motor skills (e.g., as evaluated by the Peabody Developmental Motor Scales) in a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to improve behavioral symptoms of a treated Krabbe patient (such as a juvenile or adult subject), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC) (e.g., a vector encoding GALC are amount sufficient to improve vision of a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC) (e.g., a vector encoding GALC) are amount sufficient to increase hearing of a treated Krabbe patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to increase white matter of a treated Krabbe patient (e.g., as detected by MRI of the brain or CSF opening pressure), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to reduce intracranial pressure of a treated Krabbe patient (e.g., as detected by MRI of the brain), for example by at least 10%, at least 20%, at least 25%, at least 50%, at least 70%, at least 75%, at least 80%, or at least 90% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to reduce processing time of a treated Krabbe patient (e.g., as detected by MRI of the brain), for example by at least 10%, at least 20%, at least 25%, at least 50%, at least 70%, at least 75%, at least 80%, or at least 90% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to reduce seizures of a treated Krabbe patient (e.g., as detected by MRI of the brain), for example by at least 10%, at least 20%, at least 25%, at least 50%, at least 70%, at least 75%, at least 80%, or at least 90% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to improve gait, spasticity, feeding ability, fine motor skills, adaptive function, irritability, dysautonomia, sleep, or combinations thereof, in a treated Krabbe patient (e.g., as detected by MRI of the brain), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunosuppressive agent(s), umbilical cord blood and the nucleic acid molecule encoding GALC). In one embodiment, an "effective amount" of immunosuppressive agent(s), umbilical cord blood, and nucleic acid molecule encoding GALC (e.g., a vector encoding GALC) are amount sufficient to reduce levels of CSF protein and/or reduce blood/CSF psychosine in a treated Krabbe patient (e.g., as detected by MRI of the brain), for example by at least 10%, at least 20%, at least 25%, at least 50%, at least 70%, at least 75%, at least 80%, at least 90%, at least 95%, or at least 99% (as compared to no administration of the immunosuppressive agent(s), umbilical cord blood and the nucleic acid molecule encoding GALC). In some examples, combinations of these effects are achieved.

Galactocerebrosidase (GALC): (e.g., OMIM 606890): Also known as galactosylceramidase, is an enzyme which removes galactose from ceramide derivatives (EC 3.2.1.46). Mutations in GALC, such as deletions (e.g., the 502/del mutation), insertions, and point mutations, are associated with Krabbe disease. A Y158 S mutation has been observed in dogs and a deletion of AC corresponding to cDNA positions 387 and 388 in exon 4 has been observed in rhesus monkeys.

GALC sequences are publically available, for example from the GenBank® sequence database (e.g., Accession Nos. NP_000144.2, AAH36518.1, NP_001003238.1, XP_011281775.1, AAB71823.1, and NP_001037727.1 provide exemplary GALC protein sequences, while Accession Nos.: NM_000153.3, BC036518.2, NM_001003238.1, XM_011283473.1, AH005573.2 and NM_001044262.2 provide exemplary GALC nucleic acid sequences). One of ordinary skill in the art can identify additional GALC nucleic acid and protein sequences, including GALC variants, such as those having at least 80%, at least 85%, at least 90%, at least 92%, at least 95%, at least 98%, or at least 99% sequence identity to these GenBank® sequences.

Hematopoiedc stem cell (HSC): The stem cells that give rise to all blood cells. Thus, HSCs have the ability to durably generate all blood lineages in vivo. They are present in the umbilical cord blood and bone marrow (BM). In some examples, HSCs express CD34. In some examples, HSCs express the following markers:

Mouse HSC: $CD34^{lo/-}$, $SCA-1^+$, $Flt-3^+$, $C-kit^+$, lin−
Human HSC: $CD34^+$, $CD59^+$, $Thy1/CD90^+$, $CD38^{lo/-}$, $C-kit/CD117^+$, CD166+, lin−, SLAM molecules Increase or Decrease: A statistically significant positive or negative change, respectively, in quantity from a control value (such as a value representing no therapeutic agent). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Isolated: An "isolated" biological component (such as a nucleic acid molecule or a protein) has been substantially separated, produced apart from, or purified away from other biological components in the cell or tissue of an organism in which the component occurs, such as other cells (e.g., RBCs), chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Krabbe disease: Also known as globoid cell leukodystrophy or galactosylceramide lipidosis, is a rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is caused by mutations in the GALC gene (in humans located on chromosome 14 (14q31)), which causes a deficiency of galactocerebrosidase. In addition to humans, Krabbe disease has been observed in cats, dogs (such as Westies and Cairn Terriers), and dolphins.

Symptoms of infantile Krabbe disease (e.g., patient is 0-6 months) may include irritability; hypertonia; peripheral neuropathy; vomiting and other feeding difficulties; failure to thrive; slowed development; unexplained fevers; and progressive muscle weakness, hearing loss and vision loss. Late-onset forms may not develop symptoms until later in infancy (late infantile e.g., patient is 7-12 months), childhood (late onset, e.g., patient is 13 months-10 years), early adolescence or even into adulthood (e.g., patient is 11 years or older). Signs and symptoms of these forms are variable but can include muscle weakness and rigidity; walking difficulties; vision loss; intellectual regression; and/or seizures.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a GALC coding sequence). Generally, operably linked DNA sequences are contiguous and, where necessary to join two protein coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of a therapeutic agent, such as a vector, blood cell, nucleic acid molecule, or immunosuppressive agent disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Examples of promoters include, but are not limited to the SV40 promoter, the CMV enhancer-promoter, and the CMV enhancer/β-actin promoter. Both constitutive and inducible promoters can be used in the methods provided herein (see e.g., Bitter et al., *Methods in Enzymology* 153:516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid molecule or protein sequence is one that has a sequence that is not naturally occurring or has a sequence that is made by an artificial combination of two otherwise separated segments of sequence (e.g., a viral vector that includes a GALC coding sequence). This artificial combination can be accomplished by routine methods, such as chemical synthesis or by the artificial manipulation of isolated segments of nucleic acids, such as by genetic engineering techniques. Similarly, a recombinant or transgenic cell is one that contains a recombinant nucleic acid molecule and expresses a recombinant protein.

RNA Interference (RNAi): A post-transcriptional gene silencing mechanism mediated by RNA molecules. Introduction of short RNA molecules into cells (such as double stranded RNA), results in binding of the RNA molecules to other specific messenger RNA (mRNA) molecules and can either increase or decrease their activity, for example by preventing an mRNA from producing a protein. Examples of inhibitory RNA molecules include small interfering RNA (siRNA), micro RNA (miRNA), ribozymes (such as a hammerhead ribozyme, VS ribozyme, or hairpin ribozyme), and antisense molecules. In certain examples, an RNAi molecule is directed against a target gene, such as a gene whose expression is undesirably upregulated in a subject with a genetic disease (and thus whose expression is desired to be decreased). In some examples, an RNAi molecule is at least about 19 nucleotides (nt), such as at least 20, at least 21, at least 22, at least 23, at least 24, at least 25, at least 26, or at least 27 nt in length.

Sequence identity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are. Homologs of a polypeptide will possess a relatively high degree of sequence identity when aligned using standard methods.

Methods of alignment of sequences for comparison are known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of a native GALC protein or coding sequences are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. These sequence identity ranges are provided for guidance only; it is possible that strongly significant homologs could be obtained that fall outside of the ranges provided.

Thus, a variant GALC protein or nucleic acid sequence that can be used with the methods of the present disclosure can have at least 80%, at least 85%, at least 90%, at least 91%, at least 92%, at least 93%, at least 94%, at least 95%, at least 96%, at least 97%, at least 98% or at least 99% sequence identity to SEQ ID NO: 1 or 2, as well as to any of the sequences shown in the GenBank® Accession Nos. provided herein.

Subject: A mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dolphin, dog, cat, horse, or cow. In some examples, the subject is a laboratory animal/organism, such as a mouse, rabbit, or rat. In some examples, the subject treated using the methods disclosed herein is a human infant less than 6 months of age.

In some examples, the subject has Krabbe disease, such as infantile Krabbe disease, that can be treated using the methods disclosed herein. In some examples, the subject treated using the methods disclosed herein is a human subject having a genetic disease.

Therapeutic agent: Refers to one or more molecules or compounds that confer some beneficial effect upon administration to a subject. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Transduced and Transformed: A virus or vector "transduces" a cell when it transfers nucleic acid into the cell. A cell is "transformed" or "transfected" by a nucleic acid transduced into the cell when the nucleic acid molecule becomes stably replicated by the cell, either by incorporation of the nucleic acid into the cellular genome, or by episomal replication.

Numerous methods of transfection can be used, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}.

Transgene: An exogenous gene supplied by a vector. In one example, a transgene includes a GALC coding sequence (or other therapeutic nucleic acid molecule, such as a gene, coding sequence or inhibitory RNA molecule), for example operably linked to a promoter sequence.

Transplantation: The transfer of a tissue or an organ, or cells (such as HSCs), from one body or part of the body to another body or part of the body. "Allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. "Autologous transplantation" is a transplantation of a tissue or cells from one location to another in the same individual, or transplantation of a tissue or cells from one individual to another, wherein the two individuals are genetically identical.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed methods results in a decrease in the number or severity of symptoms associated with a genetic disease, such as increasing the survival time of a treated patient with the genetic disease.

In some examples, treatment with the disclosed methods results in a decrease in the number or severity of symptoms associated with Krabbe disease, such as increasing the survival time of a treated Krabbe patient, increasing or improving myelination of cells in the CNS and/or PNS of a treated Krabbe patient, increasing or improving neurodevelopmental function in a treated Krabbe patient, increasing or improving early learning (e.g., as evaluated by the Mullen or Bayley Scales) in a treated Krabbe patient, reducing macrophage infiltration, astrogliosis, and/or CD68 expression in the CNS and/or PNS of a treated Krabbe patient, reducing tremors in a treated Krabbe patient, increasing the body weight of a treated Krabbe patient, and/or increasing or improving motor skills (e.g., as evaluated by the Peabody Developmental Motor Scales) in a treated Krabbe patient, improving feeding in a treated Krabbe patient, improving fine motor skills in a treated Krabbe patient, improving cognitive and adaptive function in a treated Krabbe patient, improving vision and hearing in a treated Krabbe patient, changing brain MRI of in a treated Krabbe patient, improving nerve conduction in a treated Krabbe patient, lowering CSF protein in a treated Krabbe patient, lowering psychosine and any biomarker of disease progression in a treated Krabbe patient, decreasing seizures in a treated Krabbe patient, reducing irritability in a treated Krabbe patient, improving sleep in a treated Krabbe patient, improving intracranial pressure in a treated Krabbe patient, improving gait in a treated Krabbe patient, and reducing behavioral problems in a treated Krabbe patient. In some examples, combinations of these effects are achieved.

Umbilical cord blood (UCB): Blood that remains in the placenta and in the attached umbilical cord after childbirth. UCB contains all the elements found in whole blood, such as red blood cells, white blood cells, plasma, platelets and hematopoietic stem cells.

Under conditions sufficient for: A phrase that is used to describe any environment that permits a desired activity. In one example the desired activity is increased expression or activity of GALC, or other protein needed to treat a disease. In one example the desired activity is treatment of or slowing the progression of a genetic disease such as Krabbe disease (or other genetic disease listed in Table 1) in vivo, for example using the disclosed methods.

Vector: A nucleic acid molecule as introduced into a host cell, thereby producing a transformed host cell. A vector may include nucleic acid sequences that permit it to replicate in the host cell, such as an origin of replication. A vector may also include a GALC coding sequence (or other therapeutic nucleic acid molecule) for example in combination with a promoter, and/or selectable marker genes, and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Overview

Krabbe disease (also called globoid cell leukodystrophy) is a rare inherited neurodegenerative disorder with an estimated incidence of 1 in 100,000 to 250,000 births. The disease is found in all races and ethnicities and is caused by mutations in the gene encoding the lysosomal enzyme galactocerebrosidase (GALC), which is essential for normal catabolism of the important galactolipid component of myelin. Deficiency of GALC activity results in the accumulation of certain galactolipids, which damage myelinating glial cells, thereby causing inflammation, rapid demyelination, and progressive deterioration of the central nervous system (CNS) and peripheral nervous system (PNS) (Wenger et al. (2013). Scriver's The Online Metabolic and Molecular Bases of Inherited Disease (OMMBID). Chapter 147 Krabbe Disease (Globoid Cell Leukodystrophy)). In the classic early-infantile form of the disease, patients present in the first 6 months of life with spasticity, developmental delay, and irritability. Loss of white matter leads to severe motor and mental deterioration and death by 2 years of age. Approximately 10% of patients have later-onset forms of the disease (late-infantile, juvenile, or adult), which can present with ataxia, weakness, vision problems, spastic paraparesis, behavioral problems, and dementia. Some genotypes lead to less severe disease with later onset, possibly related to a small amount of residual GALC activity.

Of the 147 disease-causing mutations identified in the GALC gene, some are clearly associated with early- or later-onset disease. In other cases, strong genotype-phenotype correlations are not yet well established. Most patients are diagnosed when already symptomatic unless there is family history of Krabbe disease, in which in the case infantile Krabbe disease the age at onset is similar if they share the same GALC mutations.

The current standard of care for pre-symptomatic and minimally symptomatic patients with Krabbe disease is administration of hematopoietic stem cell transplantation (HSCT), most commonly in the form of umbilical cord blood transplantation (UCBT). However, this approach has disadvantages. One major drawback is that HSCT alone has not been shown to ameliorate or slow the progression of peripheral nerve disease, which is a major cause of disability in affected individuals. Moreover, although the treatment alters the natural progression of disease, patients still deteriorate and die in their late teens (Gupta et al., *NeuroImage: Clinical.* 7:792-8, 2014). Furthermore, UCBT offers no significant benefit once a patient is already symptomatic, because of the extensive early damage to the motor tracts. Therefore, no effective treatments are available once a patient manifests signs or symptoms of Krabbe disease.

Provided herein is a novel method for treating Krabbe disease that utilizes both UCBT and gene therapy to increase expression of GALC. It is proposed that expressing GALC can correct myelination of the CNS and PNS and ameliorate the Krabbe disease phenotype better as compared to UCBT alone by shortening the interval between diagnosis and GALC availability to the nervous system. Others have proposed autologous cord blood transplantation and local lentiviral vector transfection. In contrast, in some examples the present methods use allogeneic (unrelated donor) cord blood transplantation and intravenous adeno-associated viral vector transfection to express GALC. The methods are performed in subjects that are immune suppressed, which can reduce or prevent the formation of antibodies to the GALC protein. Such methods can improve peripheral neurological functioning and prolong lifespan.

Provided herein are methods for treating Krabbe disease in a subject, such as an infant. In some examples, the method includes immunosuppressing (e.g., myelosuppressing) the subject, administering a therapeutically effective amount of umbilical cord blood (UCB) to the subject, and administering a therapeutically effective amount of a nucleic acid molecule encoding (GALC) to the subject.

Immunosuppressing the subject can include myelosuppressing or myeloablating the subject, for example by administering a therapeutically effective amount of alemtuzumab, hydroxyurea, fludarabine, and busulfan. In some examples, the method further includes administering a therapeutically effective amount of tacrolimus and mycophenolate mofetil (MMF).

In some examples, the UCB is administered prior to the nucleic acid molecule encoding GALC, such as at least 6 hours prior, at least 12 hours prior, at least 1 day prior, at least 2 days prior, at least 3 days prior, at least 4 days prior, at least 5 days prior, at least 6 days prior, or at least 7 days prior. In some examples, the UCB is allogenic to the subject, and for example matches 4, 5 or 6 of the 6 HLA markers. In some examples, administering a therapeutically effective amount of UBC includes administering a total nucleated cell dose of at least $3\times10^7$/kg adjusted ideal body weight (AIBW) to the subject.

Figure 1:
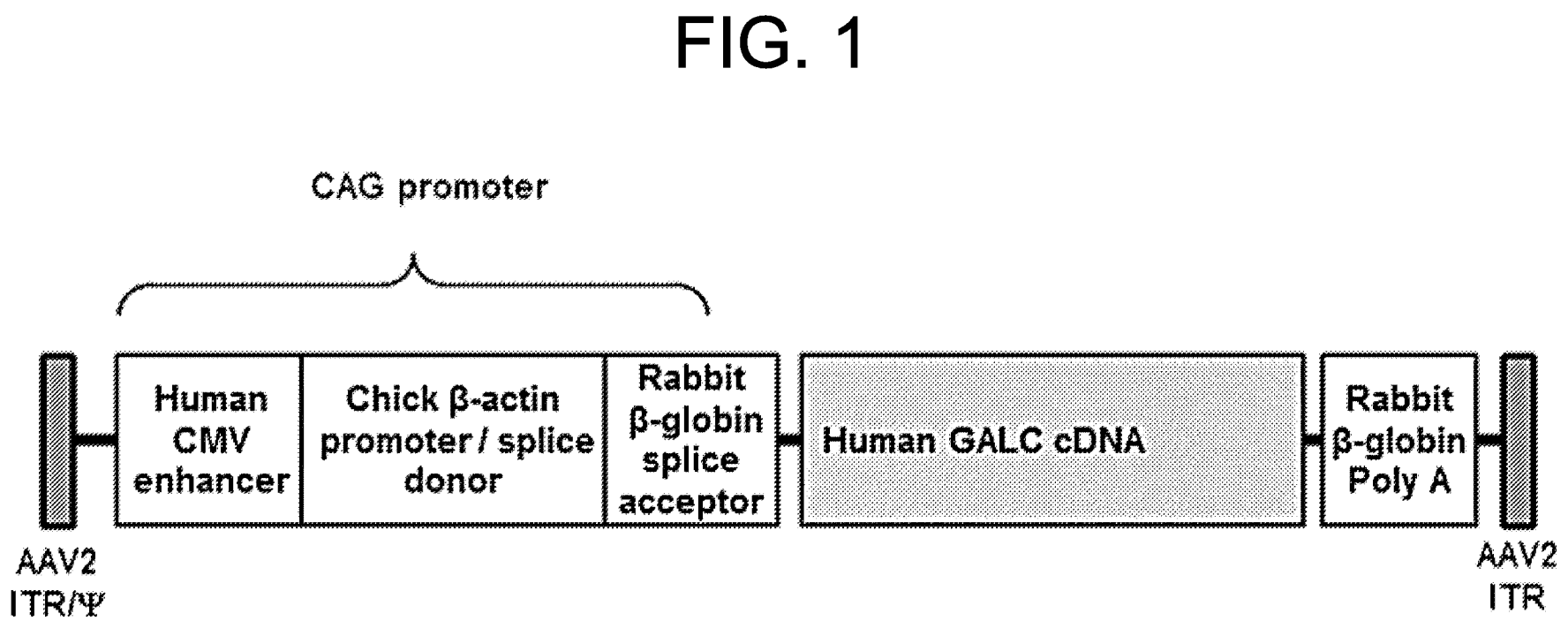

In some examples, the nucleic acid molecule encoding GALC shares at least 80%, at least 85%, at least 90%, at least 95%, at least 98%, at least 99%, or 100% sequence identity to SEQ ID NO: 1. In some examples, the nucleic acid molecule encodes a GALC protein having at least 80%, at least 85%, at least 90%, at least 95%, at least 98%, at least 99%, or 100% sequence identity to SEQ ID NO: 2. The GALC coding sequence does not include a mutation known to be associated with Krabbe disease. The nucleic acid molecule encoding GALC can be operably linked to a promoter, such as a constitutive promoter. In one example, the promoter is a CAG promoter (see FIG. 1). The nucleic acid molecule encoding GALC can be part of a vector, such as a viral vector, for example one that can cross the blood-brain barrier. In a specific example, the viral vector is an adeno-associated vector (AAV), such as AAV serotype rh.10. In some examples, the nucleic acid molecule encoding GALC is administered intravenously, for example at a dose of at least $1\times10^{11}$ genome copies (gc), at least $1\times10^{12}$ gc, at least $2\times10^{12}$ gc, at least $1\times10^{13}$ gc, at least $2\times10^{13}$ gc per subject, or at least $1\times10^{14}$ gc per subject, such as $2\times10^{11}$ gc per subject, $2\times10^{12}$ gc per subject, $2\times10^{13}$ gc per subject, or $2\times10^{14}$ gc per subject. In some examples, the nucleic acid molecule encoding GALC is administered intravenously, for example at a dose of at least $1\times10^{11}$ gc/kg, at least $5\times10^{11}$ gc/kg, at least $1\times10^{12}$ gc/kg, at least $5\times10^{12}$ gc/kg, at least $1\times10^{13}$ gc/kg, or at least $4\times10^{13}$ gc/kg, such as $4\times10^{11}$ gc/kg, $4\times10^{12}$ gc/kg, or $4\times10^{13}$ gc/kg. In some examples, the nucleic acid molecule encoding GALC is administered intravenously.

Methods of Treating Krabbe Disease

Provided herein are methods for treating Krabbe disease in a subject, such as an infant. In some examples, the method includes immunosuppressing (e.g., myelosuppressing) the subject, administering a therapeutically effective amount of umbilical cord blood (UCB) to the subject, and administering a therapeutically effective amount of a nucleic acid molecule encoding GALC to the subject (e.g., wherein the GALC does not include a mutation associated with Krabbe disease, such as a normal wt GALC nucleic acid molecule). In some examples, the method includes infusing intravenously an AAV serotype rh.10 vector carrying the GALC gene (AAVrh.10-GALC) after UCBT from an autologous donor. Such treatments can halt motor deterioration by improving myelination in the brain and peripheral nerves while the patient's immune system reconstitutes, thereby improving treatment outcomes.

Subjects

The subject to be treated can be any mammal with any form of Krabbe disease. Thus, humans, cats and dogs with early infantile Krabbe disease, late infantile Krabbe disease, or juvenile Krabbe disease, can be treated with the disclosed methods. In some examples, the subject has early infantile Krabbe disease, and is a human infant less than 6 months of age. In some examples, the subject has late infantile Krabbe disease, and is a human infant less than 1 year of age.

Immunoablation

The subject to be treated with the disclosed methods can be administered a treatment that suppresses their immune system, such as one used to suppress the immune system and/or destroy the bone marrow. Such immunoablation is performed prior to the UCBT and prior to administering the GALC coding sequence, which may reduce or eliminate an undesirable immune response. Thus, in some examples the subject to receive the UCBT and GALC coding sequence previously receives a myeloablative regimen, such as chemotherapy agents given at maximally tolerated doses expected to eradicate the hematopoietic cells in the bone marrow and resulting in profound pancytopenia within one to three weeks from the time of administration, or previously receives a non-myeloablative regimen, such as reduced doses of chemotherapy or whole body irradiation expected to partially ablate but not eliminate the recipient bone marrow. In some examples the recipient subject receives a therapy that will deplete or ablate the recipient's immune system, such as T cells, prior to receiving the UCBT and GALC coding sequence.

Examples of chemotherapeutic agents that can be used include but are not limited to: carmustine, busulfan, carboplatin, cyclophosphamide, cytoxan, etoposide, fludarabine, melphalan, methotrexate, thiotepa, topotecan, or combinations thereof. In one example, the subject is treated with a therapeutically effective amount of busulfan. In one example, the subject is treated with therapeutically effective amounts of alemtuzumab, hydroxyurea, fludarabine, and busulfan.

In some examples the subject to be treated with the methods provided herein receives irradiation, such as 1200 to 1300 centigray over three to four days, for example prior to receiving the UCBT and GALC coding sequence.

In some examples, the immunoablation includes treatment with agents that reduce graft-versus-host disease, such as a therapeutically effective amount of tacrolimus, a therapeutically effective amount of mycophenolate mofetil (MMF), or both.

Successful immunoablation is the absence of exclusively host T cell recovery. That is, as long as the T cell chimerism is not 100% host, it is successful. In some cases some host T cells are observed at ~50%, but they decline with time.

UCBT

The nomenclature for hematopoietic stem cell transplantation varies since the source differs by species. In humans bone marrow (BM) and unrelated umbilical cord blood (UCB) can be used for transplantation. However, the most rapid source of hematopoietic stem cells comes from banked cord blood unless there is a sibling donor. Therefore, the procedure for in humans can be referred to as UCBT. In mice, syngeneic bone marrow cells are utilized, and the procedure is sometimes referred to as BMT.

The UCBT (or BMT) can be performed following successful immulablation, but prior to administering the nucleic acid molecule encoding GALC. In some examples, the UCBT (or BMT) is performed at least 6 hours prior to administering the nucleic acid molecule encoding GALC, at least 12 hours prior to administering the nucleic acid molecule encoding GALC, at least 1 day prior to administering the nucleic acid molecule encoding GALC, at least 2 days prior to administering the nucleic acid molecule encoding GALC, at least 3 days prior to administering the nucleic acid molecule encoding GALC, at least 4 days prior to administering the nucleic acid molecule encoding GALC, at least 5 days prior to administering the nucleic acid molecule encoding GALC, at least 6 days prior to administering the nucleic acid molecule encoding GALC, or at least 7 days prior to administering the nucleic acid molecule encoding GALC, such as 12 hours, 24 hours, 48 hours, 72 hours, or 96 hours prior to administering the nucleic acid molecule encoding GALC. In some examples, the UCBT (or BMT) is administered IV.

In some examples, the UCB (or BM) is allogenic to the subject, In some examples, the donor has a minimum 4 of 6 HLA match with allele level HLA-DRB1 typing to the Krabbe subject to be treated, for example matches 4, 5 or 6 of the 6 HLA markers.

In some examples, the UBC (or BM) is administered at total nucleated cell (TNC) dose of at least $2\times10^7$/kg, at least $3\times10^7$/kg, such as at least $5\times10^7$/kg, at least $1\times10^8$/kg AIBW, or at least $3\times10^8$/kg AIBW. Thus, in some examples, the UBC (or BM) includes administration of at least 20 million TNC/kg, 25 million TNC/kg, 30 million TNC/kg, at least 50 million TNC/kg, at least 60 million TNC/kg, at least 70 million TNC/kg, at least 80 million TNC/kg, at least 90 million TNC/kg, at least 100 million TNC/kg, at least 100 million TNC/kg, at least 120 million TNC/kg, at least 200 million TNC/kg, or at least 250 million TNC/kg, such as 5 to $12\times10^7$ TNC/kg or 2.3 to $25\times10^7$ TNC/kg.

In some examples, the UBC (or BM) includes a CD34+ progenitor dose of at least $1.5\times10^5$/kg, such as at least $3\times10^5$/kg, at least $5\times10^5$/kg, at least $1\times10^6$/kg, at least $3\times10^6$/kg, at least $5\times10^6$/kg, at least $1\times10^7$/kg, at least $3\times10^7$/kg, at least $5\times10^7$/kg, or at least $1\times10^8$/kg, such as 1 to $9\times10^5$/kg.

The subject can also be administered granulocyte colony-stimulating factor (G-CSF), on day +1 and continued until ANC is ≥2,000. In some examples, the G-CSF is administered at a dose of at least 1 mcg/kg/dose daily IV or SC, such as at least 5 mcg/kg/dose daily IV or SC, at least 10 mcg/kg/dose daily IV or SC, or at least 10 mcg/kg/dose daily IV or SC.

Increasing GALC Expression

Nucleic acid molecules encoding functional GALC are known, and specific examples are provided herein. In some examples, the sequence of the GALC used matches the treated subject. For example, if the subject is human, a normal (e.g., non-mutated, such as one not including mutations that are associated with Krabbe disease) human GALC coding sequence can be used.

Thus, in some examples, expression of GALC in the treated subject increases GALC protein expression and/or activity in the cells of the treated subject by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, expressing GALC in the treated subject increases GALC activity (e.g., removal of galactose from ceramide derivatives) in the subject by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. For example, such increases in GALC activity may be observed in the CNS and/or PNS, such as in the brain, spinal cord, cerebellum, and/or peripheral nerves (such as the sciatic). In some examples, expressing GALC in the subject increases myelination in the CNS and/or PNS of the subject by at least 20%, at least 30%, at least 40%, at least 50%, at least 60%, at least 70%, at least 75%, at least 80%, at least 90%, at least 95%, at least 100%, at least 200%, at least 300%, at least 400%, at least 500% or at least 600%. In some examples, combinations of these effects are achieved.

In some examples, the GALC coding sequence is not part of a vector. In some examples, a GALC coding sequence is part of a vector, such as a viral vector, such as a lentiviral vector, AAV vector, or retrovirus. In some examples, expression of the GALC coding sequence is driven by a promoter, such as a constitutive promoter. In some examples, the GALC coding sequence is introduced into the subject intravenously.

In some examples, the GALC coding sequence is administered using a gene editing method, such as the CRISPR/Cas system, zinc finger nuclease (ZFN) editing, transcription activator-like effector based nuclease (TALEN) editing, and the like.

In some examples, the GALC coding sequence is administered as a naked nucleic acid molecule. In some examples, the GALC coding sequence is part of a vector (such as AAVrh.10-hGALC), and is formulated in 380 mM PBS with 5% sorbitol, for example to reduce the aggregation of the vectors and enhance penetration of blood brain barrier.

GALC Sequences

The GALC coding sequence used can be native or variant GALC sequence. Native GALC sequences are provided above via GenBank® Accession Nos. for several species. Thus, in some examples, the nucleic acid molecule encoding GALC (such as a vector containing such) introduced into the subject includes a native GALC coding sequence. In some examples, the nucleic acid molecule encoding GALC (such as a vector containing such) introduced into the subject includes a non-native GALC coding sequence, but encodes a native GALC protein sequence (e.g., a coding sequence that is degenerate).

In one example, the nucleic acid molecule encoding GALC (such as a vector containing such) encodes a variant GALC protein, including variants of the protein sequences provided above via GenBank® Accession Nos., can contain one or more mutations, such as a single insertion, a single deletion, a single substitution. However, such variations do not adversely affect the function of the protein, such as its ability to remove galactose from ceramide derivatives (e.g., include a mutation(s) associated with Krabbe disease). In some examples, the variant GALC protein includes 1-20 insertions, 1-20 deletions, 1-20 substitutions, and/or any combination thereof (e.g., single insertion together with 1-19 substitutions). In some examples, a variant GALC protein has 1, 2, 3, 4, 5, 6, 7, 8, 9, 10, 11, 12, 13, 14, 15, 16, 17, 18, 19 or 20 amino acid changes. In some examples, a variant GALC protein includes 1-8 insertions, 1-15 deletions, 1-10 substitutions, and/or any combination thereof (e.g., 1-15, 1-4, or 1-5 amino acid deletions together with 1-10, 1-5 or 1-7 amino acid substitutions. In one example, such variant peptides are produced by manipulating the nucleotide sequence encoding a peptide using standard procedures such as site-directed mutagenesis or PCR.

One type of modification includes the substitution of amino acids for amino acid residues having a similar biochemical property, that is, a conservative substitution (such as 1-4, 1-8, 1-10, or 1-20 conservative substitutions, such as 1, 2, 3, 4, 5, 6, 7, 8, 9, 10, 11, 12, 13, 14, 15, 16, 17, 18, 19 or 20 conservative substitutions). Typically, conservative substitutions have little to no impact on the activity of a resulting peptide. For example, a conservative substitution is an amino acid substitution in any native GALC protein sequence, which does not substantially affect the native function of the protein (such as removing galactose from ceramide derivatives). An alanine scan can be used to identify which amino acid residues in a GALC protein can tolerate an amino acid substitution. In one example, the native function of GALC is not altered by more than 25%, for example not more than 20%, for example not more than 10% or not more than 5%, when an alanine, or other conservative amino acid, is substituted for 1-4, 1-8, 1-10, or 1-20 native amino acids. Examples of amino acids which may be substituted for an original amino acid in a GALC protein and which are regarded as conservative substitutions include: Ser for Ala; Lys, Gln, or Asn for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Nucleic acid molecules encoding a native or variant GALC protein can be incorporated into a vector. Nucleic acid sequences coding for a native or variant GALC such as those having at least 90%, at least 92%, at least 95%, at least 96%, at least 97%, at least 98%, or at least 99% sequence identity to those shown in a GenBank® Accession No. provided herein (for example to SEQ ID NO: 1 or 2), can be generated. In addition, a variety of clones containing functionally equivalent nucleic acids, such as nucleic acids which differ in sequence but which encode the same protein sequence, can be generated. In some examples, such a GALC coding sequence is optimized for expression in a host cell.

Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA.

Codon preferences and codon usage tables for a particular species can be used to engineer isolated nucleic acid molecules encoding a GALC protein that take advantage of the codon usage preferences of that particular species. For example, the GALC protein expressed from a vector) can be designed to have codons that are preferentially used by a particular organism of interest (e.g., in a mammal with Krabbe disease).

A nucleic acid encoding a GALC protein can be cloned or amplified by in vitro methods, such as the polymerase chain reaction (PCR), the ligase chain reaction (LCR), the transcription-based amplification system (TAS), the self-sustained sequence replication system (3SR) and the Q0 replicase amplification system (QB). A wide variety of cloning and in vitro amplification methodologies can be used. In addition, nucleic acids encoding sequences encoding a GALC protein can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding a GALC protein can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, a GALC protein is prepared by inserting the cDNA which encodes the GALC protein into a vector. The insertion can be made so that the protein(s) is read in frame so that the protein(s) is produced. Techniques for preparing recombinant vectors (e.g., plasmid or virus) containing a heterologous nucleic acid sequence encoding the GALC protein are known.

The nucleic acid coding sequence for a GALC protein can be inserted into an expression vector including, but not limited to a plasmid, virus or other vehicle that can be manipulated to allow insertion or incorporation of sequences and can be expressed in a subject with Krabbe disease. Methods of expressing coding sequences from a vector are known. Biologically functional viral and plasmid DNA vectors capable of expression and replication in a T cell are known. The expression vector can contain additional elements necessary for the transfer and subsequent replication of the expression vector containing the GALC protein coding sequence in the T cell. Examples of such elements include, but are not limited to, origins of replication and selectable markers, such as a thymidine kinase gene or an antibiotic resistance marker.

Nucleic acid sequences encoding a GALC protein can be operatively linked to expression control sequences, such as a promoter. An expression control sequence operatively linked to a GALC protein coding sequence is ligated such that expression of the GALC protein coding sequence is achieved under conditions compatible with the expression control sequences. Exemplary expression control sequences include, but are not limited to appropriate promoters, enhancers, transcription terminators, a start codon (i.e., ATG) in front of a GALC protein-encoding gene, splicing signal for introns, maintenance of the correct reading frame of that gene to permit proper translation of mRNA, and stop codons. Examples of expression control elements that can be used include, but are not limited to, lac system, operator and promoter regions of phage lambda, and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the GALC protein in the host cell. In one example, the promoter includes a human CMV enhancer, beta-acting promoter, beta-globin splice acceptor, or combinations thereof (e.g., see FIG. 1, CAG promoter). In some examples, two or three promoters are used.

Exemplary Viral Vectors

Viral vectors can be prepared that encode a GALC protein. Exemplary viral vectors that can be used include, but are not limited to, polyoma, SV40, adenovirus, vaccinia virus, adeno-associated virus (AAV), herpes viruses including HSV and EBV, Sindbis viruses, alphaviruses and retroviruses of avian, murine, and human origin. Baculovirus (*Autographa californica* multinuclear polyhedrosis virus; AcMNPV) vectors can also be used. Other suitable vectors include orthopox vectors, avipox vectors, fowlpox vectors, capripox vectors, suipox vectors, lentiviral vectors, alpha virus vectors, and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

In some examples, the GALC coding sequence is part of a vector, such as one that can penetrate the blood-brain barrier, for example following intravenous administration. Examples of such vectors include adeno-associated viruses (AAVs), such as AAV serotypes AAV9 and AAVrh.10. The adeno-associated virus serotype rh.10 (AAV.rh10) vector partially penetrates the blood-brain barrier, provides high levels and spread of transgene expression (Sondhi et al., *Mol Ther.* 15(3):481-91, 2007; De et al., *Mol Ther.* 13:67-76, 2006), and appears to transduce neurons, astrocytes, and glial cells following intravenous delivery (Zhang et al., *J. Virol. Methods* 179:276-80, 2011).

The sequence of an exemplary AAV.rh10 capsid that can be used in the disclosed methods is provided in SEQ ID NO: 3 (another example is provided in SEQ ID NO: 59 of EP 2341068). Thus, in some examples, the AAV.rh10 vector used has at least 90%, at least 92%, at least 95%, at least 96%, at least 97%, at least 98%, or at least 99% sequence identity to SEQ ID NO: 3, or encodes a protein having at least 90%, at least 92%, at least 95%, at least 96%, at least 97%, at least 98%, or at least 99% sequence identity to SEQ ID NO: 4. AAV.rh10 includes of an AAV2 gene transfer vector backbone (inverted terminal repeats of AAV2 flanking the expression cassette); an expression cassette with a human cytomegalovirus enhancer, promoter, splice donor, and left-hand intron sequence from chicken ß-actin; right-hand intron sequence and splice acceptor from rabbit ß-globin (this enhancer/promoter/intron sequence is referred to as "CAG"). The CAG promoter is a strong ubiquitous promoter used to drive gene expression in AAV vectors. The AAV.rh10-hGALC vector further includes a full-length human GALC cDNA; and a rabbit β-globin polyA sequence (FIG. 1). The single-stranded genome will be packaged in the capsid of AAV serotype rh.10, which was originally isolated from the rhesus macaque (Gao et al., *Proc Natl Acad Sci USA.* 99(18):11854-9, 2002). One skilled in the art will appreciate that the full-length human GALC cDNA can be replaced with the GALC cDNA from any mammal of interest, depending on the subject treated. Thus, for example, a dog treated for Krabbe disease can utilize an AAV.rh10-GALC vector that includes a full-length dog GALC cDNA in place of the full-length human GALC cDNA. A lowercase letter before the gene abbreviation in the vector name can be used to indicate the species that is the source of transgene, for example: AAVrh.10-mGALC=mouse cDNA and AAVrh.10-hGALC=human cDNA.

The sequence of an exemplary AAV.rh10 capsid sequence which can be part of a vector is provided in SEQ ID NO: 3. Thus, in some examples, the AAV.rh10 used has at least 90%, at least 92%, at least 95%, at least 96%, at least 97%, at least 98%, at least 99%, or 100% sequence identity to SEQ ID NO: 3. In some examples, the AAV.rh10 used encodes a protein having at least 90%, at least 92%, at least 95%, at least 96%, at least 97%, at least 98%, at least 99%, or 100% sequence identity to SEQ ID NO: 4.

In some examples, the vector (such as AAVrh.10-hGALC) is formulated in 380 mM PBS with 5% sorbitol, for example to reduce the aggregation of the vectors and enhance penetration of blood brain barrier.

In some examples, the nucleic acid molecule encoding GALC is administered intravenously, for example at a dose of at least $1 \times 10^{11}$ genome copies (gc, sometimes called vector genomes (vg)), such as at least $2 \times 10^{11}$ gc, $1 \times 10^{12}$ gc, at least $2 \times 10^{12}$ gc, at least $1 \times 10^{13}$ gc, at least $2 \times 10^{13}$ gc per subject, or at least $1 \times 10^{14}$ gc per subject, such as $2 \times 10^{11}$ gc per subject, $2 \times 10^{12}$ gc per subject, $2 \times 10^{13}$ gc per subject, or $2 \times 10^{14}$ gc per subject. In some examples, the nucleic acid molecule encoding GALC is administered intravenously, for example at a dose of at least $1 \times 10^{11}$ gc/kg, at least $5 \times 10^{11}$ gc/kg, at least $1 \times 10^{12}$ gc/kg, at least $5 \times 10^{12}$ gc/kg gc per subject, at least $1 \times 10^{13}$ gc/kg, at least $5 \times 10^{13}$ gc/kg, or at least $a \times 10^{14}$ gc/kg, such as $4 \times 10^{11}$ gc/kg, $4 \times 10^{12}$ gc/kg, or $4 \times 10^{13}$ gc/kg.

If adverse symptoms develop, such as AAV-capsid specific T cells in the blood, corticosteroids can be administered (e.g., see Nathwani et al., *N Engl J Med.* 365(25):2357-65, 2011).

Immunoablation and Transplantation Prior to Gene Therapy

Provided herein are methods of treating a subject with a disease resulting from a genetic mutation (such as deletion, insertion, or substitution of one or more nucleotides, or combinations thereof). The disclosed methods reduce or prevent an immune response (e.g., antibody development) against the reagents used in gene therapy (such as a viral vector or portion thereof, or a protein not previously expressed by the subject). Such methods can increase the success of gene therapy. The disclosed methods include ablating the subject's bone marrow, transplanting the patient with hematopoietic stem cells (HSCs) (which will reconstitute the subject with an immune system), and administering the gene therapy after the HSC transplant.

In one embodiment, an "effective amount" of immunoablation agent(s), HSCs, and nucleic acid molecule encoding a therapeutic nucleic acid molecule (e.g., a vector encoding a therapeutic nucleic acid molecule) are amounts sufficient to increase the survival time of a treated patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the immunoablation agent(s), HSCs, and nucleic acid molecule encoding a therapeutic nucleic acid molecule). In one embodiment, an "effective amount" of immunoablation agent(s), HSCs, and nucleic acid molecule encoding a therapeutic nucleic acid molecule (e.g., a vector encoding a therapeutic nucleic acid molecule) are amounts sufficient to increase the survival time of a treated patient, for example by at least 6 months, at least 9 months, at least 1 year, at least 1.5 years, at least 2 years, at least 2.5 years, at least 3 years, at least 4 years, at least 5 years, at least 10 years, at least 12 years, at least 15 years, or at least 20 years (as compared to no administration of the immunoablation agent(s), HSCs, and nucleic acid molecule encoding a therapeutic nucleic acid molecule).

In some examples, an "effective amount" of immunoablation agent(s), HSCs, and nucleic acid molecule encoding a therapeutic nucleic acid molecule (e.g., a vector encoding a therapeutic nucleic acid molecule) are amounts sufficient to reduce an immune response to gene therapy in a treated patient, for example by at least 10%, at least 20%, at least 25%, at least 50%, at least 70%, at least 75%, at least 80%, at least 90%, at least 95%, at least 99%, or at least 100%, (as compared to no administration of the immunoablation agent (s), HSCs, and nucleic acid molecule encoding a therapeutic nucleic acid molecule). In some examples, the reduction in immune response to the gene therapy is measured by monitoring antibody production against the therapeutic protein, vector components, or both.

Thus, the disclosed methods can increase the survival time of a treated patient, reduce an immune response to gene therapy, or both.

Subjects

The subject to be treated can be any vertebrate, such as a bird or mammal, with any genetic disease, such as those listed in Table 1. Thus, humans, monkeys, cats, dogs or other veterinary subject with a genetic disease can be treated with the disclosed methods. In some examples, the subject is a human infant less than 6 months of age. In some examples, the subject is a human adult at least 18 years of age.

Full or Partial Myeloablation

In some examples, prior to receiving a bone marrow transplant (such as with HSCs) and gene therapy, the subject receives myeloablative therapy in an amount that eradicates hematopoietic cells in the bone marrow. Such methods suppress the subject's immune system and destroy their bone marrow. This treatment results in profound pancytopenia within one to three weeks from the time of administration. Such treatment can be used to reduce or eliminate immune reactions against the subsequently administered gene therapy. In some examples, chemotherapy, irradiation, or both, are used to myeloablate the subject.

In some examples, subject is administered a therapeutically effective amount of total body irradiation (TBI), chemotherapy, or combinations thereof. Examples of chemotherapeutic agents that can be used include but are not limited to one or more of: carmustine, busulfan (Bu), carboplatin, cyclophosphamide (Cy), cytoxan, etoposide, fludarabine, hydroxyurea, melphalan, methotrexate, thiotepa, and topotecan. In one example, the subject is treated with a therapeutically effective amount of busulfan. In one example, the subject is treated with therapeutically effective amounts of alemtuzumab, hydroxyurea, fludarabine, and busulfan. In one example, the subject is treated with a therapeutically effective amount of alemtuzumab and fludarabine (e.g., 0.2 to 5 mg/kg iv alemtuzumab, 0.1 to 30 mg/kg iv fludarabine), which in some examples further includes hydroxyurea (e.g., 30 mg/kg/day oral), Bu, melphalan (e.g., 70 mg/kg/dose IV), thiotepa (e.g., 200 mg/kg/dose IV) or combinations thereof. In some examples, the method further includes administering a therapeutically effective amount of tacrolimus and mycophenolate mofetil (MMF).

In some examples the subject to be treated receives irradiation, such as 1200 to 1300 centigray over three to four days. In one example, the subject is administered 1 mg/kg oral Bu every 6 h for 16 total doses (16 mg/kg), followed by 2-4 days Cy for a total of 120-200 mg/kg. In some examples, the subject is administered 120 mg/kg Cy with six fractionated doses of irradiation at 200 cGy.

Successful myeloablation is the absence of exclusively host T cell recovery. That is, as long as the T cell chimerism is not 100% host, it is successful. In some cases some host T cells are observed at ~50%, but they decline with time.

In some examples, prior to receiving a bone marrow transplant (such as with HSCs) and gene therapy, the subject receives a non-myeloablative therapy in an amount that reduces, but does not eradicate, hematopoietic cells in the bone marrow. Thus, such subjects can receive reduced doses of chemotherapy or whole body irradiation expected to partially ablate but not eliminate the recipient bone marrow. In one example, a non-myeloablative treatment does not use busulfan, but instead uses melphalan and thiotepa (for example as described in NIH clinical trial NCT01962415 (clinicaltrials.gov/show/NCT01962415) herein incorporated by reference in its entirety. In some examples, melphalan is administered IV at 70 mg/m2/dose and thiotepa is administered IV administration at 200 mg/m2/dose.

Infusion of HSCs

After the subject has received myeloablative therapy, the subject is administered a therapeutically effective amount of cells to regenerate the bone marrow, such as HSCs (e.g., allogenic HSCs). Such methods regenerate the subject's immune system following myeloablative therapy. HSCs are stem cells that give rise to all blood cells. Thus, HSCs can generate all blood lineages in vivo. They are present in the umbilical cord, blood, and bone marrow (BM). In some examples, HSCs express CD34. In some examples, mouse HSC are CD34lo/−, SCA-1+, Flt-3+, C-kit+, lin−. In some examples, human HSC are CD34+, CD59+, Thy1/CD90+, CD38lo/−, C-kit/CD117+, CD166+, lin−.

In some examples, the subject is administered bone marrow (BM), unrelated umbilical cord blood, banked cord blood, or HSCs (such as those obtained from umbilical cord, blood (such as PBMCs), or BM). The transplant is performed following successful myeloablation, but prior to administering the nucleic acid molecule for gene therapy.

In some examples, the transplant including HSCs is performed at least 6 hours, prior to administering the nucleic acid molecule for gene therapy, at least 12 hours to administering the nucleic acid molecule for gene therapy, such as at least 1 day, at least 2 days, at least 3 days, at least 4 days, at least 5 days, at least 6 days, at least 7 days, at least 2 weeks, at least 3 weeks, at least 1 month, or at least 2 months prior to administering the nucleic acid molecule for gene therapy, such as 12 hours, 24 hours, 48 hours, 72 hours, or 96 hours prior to administering the nucleic acid molecule for gene therapy. In some examples, the transplant including HSCs is administered IV.

In some examples, the HSCs are allogenic to the subject. In some examples, the donor has a minimum 4 of 6 HLA match with allele level HLA-DRB1 typing to the subject to be treated, for example matches 4, 5 or 6 of the 6 HLA markers. In some examples, the HSCs are autologous to the subject.

In some examples, the subject receives total nucleated cell (TNC) dose of at least $2 \times 10^7$/kg, at least $3 \times 10^7$/kg, such as at least $5 \times 10^7$/kg, at least $1 \times 10^8$/kg AIBW, or at least $3 \times 10^8$/kg AIBW. Thus, in some examples, the subject is administered at least 20 million TNC/kg, 25 million TNC/kg, 30 million TNC/kg, at least 50 million TNC/kg, at least 60 million TNC/kg, at least 70 million TNC/kg, at least 80 million TNC/kg, at least 90 million TNC/kg, at least 100 million TNC/kg, at least 100 million TNC/kg, at least 120 million TNC/kg, at least 200 million TNC/kg, or at least 250 million TNC/kg, such as 5 to $12 \times 10^7$ TNC/kg or 2.3 to $25 \times 10^7$ TNC/kg.

In some examples, the subject receives a CD34+ progenitor dose of at least $1.5 \times 10^5$/kg, such as at least $3 \times 10^5$/kg, at least $5 \times 10^5$/kg, at least $1 \times 10^6$/kg, at least $3 \times 10^6$/kg, at least $5 \times 10^6$/kg, at least $1 \times 10^7$/kg, at least $3 \times 10^7$/kg, at least $5 \times 10^7$/kg, or at least $1 \times 10^8$/kg, such as 1 to $30 \times 10^5$/kg, such as 1.5 to $30 \times 10^5$/kg.

The subject can also be administered granulocyte colony-stimulating factor (G-CSF), on day +1 and continued until ANC is ≥2,000. In some examples, the G-CSF is administered at a dose of at least 1 mcg/kg/dose daily IV or SC, such as at least 5 mcg/kg/dose daily IV or SC, at least 10 mcg/kg/dose daily IV or SC, or at least 10 mcg/kg/dose daily IV or SC.

In some examples, following the transplant, the subject receives immunosuppressive therapy until their immune system recovers. In some examples, the subject is administered a therapeutically effective amount of one or more immunosuppressive agents, such as a calcineurin inhibitor (e.g., tacrolimus, cyclosporine A), glucocorticoid (e.g., prednisone, dexamethasone, hydrocortisone) or a cytostatic agent (e.g., methotrexate, azathioprine, cytotoxic antibiotics). In some examples, the subject is administered a therapeutic amount of cyclophosphamide following the transplant.

Administration of Gene Therapy

Following immunoablation and associated complete or partial myelablation, HSCs (e.g., cord blood or bone marrow) are transplanted to rebuild the treated subject's hematopoietic and immune system, a therapeutically effective amount of a therapeutic nucleic acid molecule is administered to the subject, wherein the nucleic acid molecule corrects the genetic disease. In some examples, the therapeutic nucleic acid molecule is part of a viral vector, such as an AAV vector (such as AAV.rh10), adenoviral vector, or a lentiviral vector. Other examples are provided herein (also see Choudhury et al., *Neuropharmacol.* 120:63-80, 2017, herein incorporated by reference in its entirety). The methods are not limited to particular gene therapy methods, and include those that utilize non-homologous end joining (NHEJ), zinc finger nuclease (ZFNs), transcriptional activator like effector nucleases, (TALEN), and CRISPR/Cas9 (see for example Morgan et al., *Cell Stem Cell* 21:574-90, 2017; Shim et al., *Acta Pharma. Sinica* 38:738-53, 2017, herein incorporated by reference in their entireties).

Examples of gene therapy include those methods and agents used to increase expression of a gene or protein, decrease expression of a gene or protein, or correct a gene or protein sequence. For example, to induce gene expression, a functional gene can be delivered to the subject, for example to target cells or tissues that lack the normal function. To reduce gene expression, a short nucleic acid molecule (such as an siRNA, antisense molecule) can be introduced to silence or interfere with the disease-related gene. Gene editing methods can be used to exert permanent and specific proofreading effects at the genome level.

Diseases that can be treated with the disclosed methods include any genetic disease of the blood (e.g. sickle cell disease, primary immunodeficiency diseases), HIV (such as HIV-1), and hematologic malignancies or cancers. Examples of primary immunodeficiency diseases and their corresponding mutations include those listed in Al-Herz et al. (*Frontiers in Immunology*, volume 5, article 162, Apr. 22, 2014, herein incorporated by reference in its entirety). Hematologic malignancies or cancers are those tumors that affect blood, bone marrow, and lymph nodes. Examples include leukemia (e.g., acute lymphoblastic leukemia, acute myelogenous leukemia, chronic lymphocytic leukemia, chronic myelogenous leukemia, acute monocytic leukemia), lymphoma (e.g., Hodgkin's lymphoma and non-Hodgkin's lymphoma), and myeloma. Table 1 provides a list of exemplary disorders and genes that can be targeted by the therapeutic nucleic acid molecules. In some examples, mutations that can be corrected by gene editing are provided.

TABLE 1

| Exemplary disorders and corresponding mutations | | |
|---|---|---|
| Disease | Gene | Mutation |
| Blood cell disorder | | |
| sickle cell anemia | β-globin chain of hemoglobin | SNP (A to T) that gives rise to point mutation (Glu–>Val at $6^{th}$ aa) |
| hemophilia | any of clotting factors I through XIII | |
| hemophilia A | clotting factor VIII | large deletions, insertions, inversions, and point mutations |
| hemophilia B | clotting factor IX | |
| Alpha-Thalassemia | HBA1 or HBA2 | Mutation or a deletion in chromosome 16 p |
| Beta-Thalassemia | HBB | Mutations in chromosome 11 |
| Delta-Thalassemia | HBD | mutation |
| von Willebrand Disease | von Willebrand factor | mutations or deletion |
| pernicious anemia | MTHFR | |
| Fanconi anemia | FANCA, FANCC, FANCD2, FANCG, FANCJ | FANCA: c.3788_3790del (p.Phe1263del); c.1115_1118delTTGG (p.Val372fs); Exon 12-17del; Exon 12-31del; c.295C > T (p.Gln99X) FANCC: c.711 + 4A > T (originally reported as IVS4 + 4A > T); c.67delG (originally reported as 322delG) FANCD2: c.1948 – 16T > G FANCG; c.313G > T (p.Glu105X); |

TABLE 1-continued

| Exemplary disorders and corresponding mutations | | |
| --- | --- | --- |
| Disease | Gene | Mutation |
| | | c.1077 − 2A > G; c.1480 + 1G > C; c.307 + 1G > C; c.1794_1803del (p.Trp599fs); c.637_643del (p.Tyr213fs) FANCJ: c.2392C > T (p.Arg798X) |
| Thrombocytopenic purpura | ADAMTS13 | Missense and nonsense mutations |
| thrombophilia | Factor V Leiden Prothrombin | Mutation in the F5 gene at position 1691 Prothrombin G20210A |
| Primary Immunodeficiency Diseases | | |
| T-B+ SCID | IL-2RG, JAK3, defect in gamma chain of receptors for IL-2, -4, -7, -9, -15 and -21 | |
| T-B− SCID | RAG1, RAG2 | |
| WHIM syndrome | CXCR4 | heterozygous mutations (e.g., in the carboxy-terminus); carboxy-terminus truncation (e.g., 10-19 residues) |
| Other Primary immune deficiency (PID) syndromes | | |
| IL-7 receptor severe combined immune deficiency (SCID) | IL7 receptor | |
| Adenosine deaminase deficiency (ADA) SCID | ADA | |
| Purine nucleoside phosphorylase (PNP) deficiency | PNP | |
| Wiskott-Aldrich syndrome (WAS) | WAS | More than 300 mutations identified |
| Chronic granulomatous disease (CGD) | CYBA, CYBB, NCF1, NCF2, or NCF4 | |
| Leukocyte adhesion deficiency (LAD) | Beta-2 integrin | |
| HIV | C-C chemokine receptor type 5 (CCR5), MSRB1 HIV long terminal repeats CSCR4 P17 PSIP1 | Deletion of 32 bp in CCR5 |
| Duchenne muscular dystrophy | CCR5 DMD | |
| Glycogen storage disease type IA | G6Pase | |
| Retinal Dystrophy | CEP290 ABCA4 | C2991 + 1655A > G 5196 + 1216C > A; 5196 + 1056A > G; 5196 + 1159G > A; 5196 + 1137G > A; 938 − 619A > G; 4539 + 2064C > T |
| X-linked immunodeficiency with magnesium defect, Epstein-Barr virus infection, and neoplasia (XMEN) | MAGT1 | |
| MonoGenetic Disorders | | |
| Metachromatic leukodystrophy (MLD) | arylsulfatase A (ARSA) | |
| Adrenoleukodystrophy (ALD) | ABCD1 | |
| Mucopolysaccaridoses (MPS) disorders | IDS | |
| Hunter syndrome | IDUA | |
| Hurler syndrome | IDUA | |
| Scheie syndrome | SGSH, NAGLU, HGSNAT, GNS | |
| Sanfilippo syndrome A, B, C, and D | GALNS | |
| | GLB1 | |
| Morquio syndrome A | ARSB | |

TABLE 1-continued

Exemplary disorders and corresponding mutations

| Disease | Gene | Mutation |
|---|---|---|
| Morquio syndrome B | GUSB | |
| Maroteaux-Lamy syndrome | HYAL1 | |
| Sly syndrome | | |
| Natowicz syndrome | | |
| Alpha manosidosis | MAN2B1 | |
| Nieman Pick disease types A, B, and C | SMPD1, NPC1, NPC2 | |
| Cystic fibrosis | cystic fibrosis transmembrane conductance regulator (CFTR) | ΔF508 |
| Polycystic kidney disease | PKD-1, PDK-2, PDK-3 | |
| Tay Sachs Disease | HEXA | 1278insTATC |
| Gaucher disease | GBA | |
| Huntington's disease | HTT | CAG repeat |
| Neurofibromatosis types 1 and 2 | NF-1 and NF2 | CGA->UGA->Arg1306Term in NF1 |
| Familial hypercholesterolemia | APOB, LDLR, LDLRAP1, and PCSK9 | |
| Cancers | | |
| Chronic myeloid leukemia (CML) | BCR-ABL ASXL1 | fusion |
| Acute myeloid leukemia (AML) | Chromosome 11q23 or t(9; 11) | translocation |
| Osteosarcoma | RUNX2 | |
| Colorectal cancer | EPHA1 | |
| Gastric cancer, melanoma | PD-1 | |
| Prostate cancer | Androgen receptor | |
| Cervical cancer | E6, E7 | |
| Glioblastoma | CD | |
| Neurological disorders | | |
| Alzheimer's disease | NGF | |
| Metahchromatic leukodystrophy | ARSA | |
| Multiple sclerosis | MBP | |
| Wiskott-Aldrich syndrome | WASP | |
| X-linked adrenoleukodystrophy | ABCD1 | |
| AACD deficiency | AADC | |
| Batten disease | CLN2 | |
| Canavan disease | ASPA | |
| Giant axonal neuropathy | GAN | |
| Leber's hereditary optic neuropathy | MT-ND4 | |
| MPS IIIA | SGSH, SUMF1 | |
| Parkinson's disease | GAD, NTRN, TH, AADC, CH1, GDNF, AADC | |
| Pompe disease | GAA | |
| Spinal muscular atrophy type 1 | SMN | |

Using the disclosed methods can be used to treat any of the disorders listed in Table 1, or other known genetic disorder. Treatment does not require 100% removal of all characteristics of the disorder, but can be a reduction in such. Although specific examples are provided below, based on this teaching one will understand that symptoms of other disorders can be similarly affected. For example, the disclosed methods can be used to increase expression of a protein that is not expressed or has reduced expression by the subject, decrease expression of a protein that is undesirably expressed or has reduced expression by the subject, correct a genetic mutation, or combinations thereof.

For example, the disclosed methods can be used to treat or reduce the undesirable effects of a genetic disease of the blood, such as a primary immunodeficiency disease.

For example, the disclosed methods (which can use a therapeutic nucleic acid molecule to correct a mutation in the β-globin chain of hemoglobin) can treat or reduce the undesirable effects of sickle cell disease. In one example, the therapeutic nucleic acid molecule can correct a mutation in the β-globin chain of hemoglobin that results in the sickle-cell disease. In one example the disclosed methods reduce the symptoms of sickle-cell disease in the recipient subject (such as one or more of, presence of sickle cells in the blood, pain, ischemia, necrosis, anemia, vaso-occlusive crisis, aplastic crisis, splenic sequestration crisis, and haemolytic crisis) for example a reduction of at least 10%, at least 20%, at least 50%, at least 70%, or at least 90% (as compared to no administration of the therapeutic nucleic acid molecule). In one example the disclosed methods decrease the number of sickle cells in the recipient subject, for example a decrease of at least 10%, at least 20%, at least 50%, at least 70%, at least 90%, or at least 95% (as compared to no administration of the therapeutic nucleic acid molecule).

For example, the disclosed methods (which can use a therapeutic nucleic acid molecule to correct a mutation in the factor V Leiden or prothrombin gene) can treat or reduce the undesirable effects of thrombophilia. In one example, the therapeutic nucleic acid molecule can correct a mutation in the factor V Leiden or prothrombin gene that results in the thrombophilia. In one example the disclosed methods reduce the symptoms of thrombophilia in the recipient subject (such as one or more of, thrombosis, such as deep vein thrombosis, pulmonary embolism, venous thromboembolism, swelling, chest pain, palpitations) for example a reduction of at least 10%, at least 20%, at least 50%, at least 70%, or at least 90% (as compared to no administration of the therapeutic nucleic acid molecule). In one example the disclosed methods decrease the activity of coagulation factors in the recipient subject, for example a decrease of at least 10%, at least 20%, at least 50%, at least 70%, at least 90%, or at least 95% (as compared to no administration of the therapeutic nucleic acid molecule).

For example, the disclosed methods (which can use a therapeutic nucleic acid molecule to correct a mutation in the CD40 ligand gene) can be used to treat or reduce the undesirable effects of CD40 ligand deficiency. In one example, the therapeutic nucleic acid molecule can correct a mutation in the CD40 ligand gene that results in the CD40 ligand deficiency. In one example the disclosed methods reduce the symptoms of CD40 ligand deficiency in the recipient subject (such as one or more of, elevate serum IgM, low serum levels of other immunoglobulins, opportunistic infections, autoimmunity and malignancies) for example a reduction of at least 10%, at least 20%, at least 50%, at least 70%, or at least 90% (as compared to no administration of the therapeutic nucleic acid molecule s). In one example the disclosed methods increase the amount or activity of CD40 ligand deficiency in the recipient subject, for example an increase of at least 10%, at least 20%, at least 50%, at least 70%, at least 90%, at least 100%, at least 200% or at least 500% (as compared to no administration of the therapeutic nucleic acid molecule).

For example, the disclosed methods (which can use a therapeutic nucleic acid molecule to decrease CCR5 activity) can be used to treat or reduce the undesirable effects of HIV-1 infection. In one example, the therapeutic nucleic acid molecule can decrease CCR5 activity, such as a decrease of at least 20%, at least 50%, at least 70% or at least 90%. In one example, the CCR5 is modified to include a 32-bp deletion (CCR5Δ32). In one example the disclosed methods reduce the symptoms of HIV-1 infection in the recipient subject (such as one or more of, fever, large tender lymph nodes, throat inflammation, a rash, headache, sores of the mouth, nausea, vomiting, diarrhea, peripheral neuropathy, Guillain-Barre syndrome, weight loss, viral load, decreased levels of CD4+ T cells, *pneumocystis* pneumonia, cachexia in the form of HIV wasting syndrome and esophageal candidiasis) for example a reduction of at least 10%, at least 20%, at least 50%, at least 70%, or at least 90% (as compared to no administration of the therapeutic nucleic acid molecule). In one example the disclosed methods increase levels of CD4+ T cells in the HIV-infected recipient subject, for example an increase of CD4+ T cells of at least 10%, at least 20%, at least 50%, at least 70%, at least 90%, at least 100%, at least 200%, at least 500% or at least 1000% (as compared to no administration of the therapeutic nucleic acid molecule).

For example, the disclosed methods can be used to treat or reduce the undesirable effects of a primary immunodeficiency disease resulting from a genetic defect. For example, the disclosed methods (which can use a therapeutic nucleic acid molecule to correct a mutation in a gene listed above, or can express a functional protein missing or defective in the subject) can treat or reduce the undesirable effects of a primary immunodeficiency disease. In one example the disclosed methods reduce the symptoms of a primary immunodeficiency disease in the recipient subject (such as one or more of, a bacterial infection, fungal infection, viral infection, parasitic infection, lymph gland swelling, spleen enlargement, wounds, and weight loss) for example a reduction of at least 10%, at least 20%, at least 50%, at least 70%, or at least 90% (as compared to no administration of the therapeutic nucleic acid molecule). In one example the disclosed methods increase the number of immune cells (such as T cells, such as CD8 cells) in the recipient subject with a primary immune deficiency disorder, for example an increase of at least 10%, at least 20%, at least 50%, at least 70%, at least 90%, at least 95%, at least 100%, at least 200%, at least 300%, at least 400%, or at least 500% (as compared to no administration of the therapeutic nucleic acid molecule). In one example the disclosed methods reduce the number of infections ((such as bacterial, viral, fungal, or combinations thereof) in the recipient subject over a set period of time (such as over 1 year) with a primary immune deficiency disorder, for example a decrease of at least 10%, at least 20%, at least 50%, at least 70%, at least 90%, or at least 95%, (as compared to no administration of the therapeutic nucleic acid molecule).

For example, the disclosed methods can be used to treat or reduce the undesirable effects of a monogenetic disorder. For example, the disclosed methods (which can use a therapeutic nucleic acid molecule to correct a mutation in a gene listed above, or can express a functional protein missing or defective in the subject) can treat or reduce the undesirable effects of a monogenetic disorder. In one example the disclosed methods reduce the symptoms of a monogenetic disorder in the recipient subject, for example a reduction of at least 10%, at least 20%, at least 50%, at least 70%, or at least 90% (as compared to no administration of the therapeutic nucleic acid molecule). In one example the disclosed methods increase the amount of normal protein not normally expressed by the recipient subject with a p monogenetic disorder, for example an increase of at least 10%, at least 20%, at least 50%, at least 70%, at least 90%, at least 95%, at least 100%, at least 200%, at least 300%, at least 400%, or at least 500% (as compared to no administration of the therapeutic nucleic acid molecule).

For example, the disclosed methods can be used to treat or reduce the undesirable effects of a hematological malignancy in the recipient subject. In one example the disclosed methods reduce the number of abnormal white blood cells (such as B cells) in the recipient subject (such as a subject with leukemia), for example a reduction of at least 10%, at least 20%, at least 50%, at least 70%, or at least 90% (as compared to no administration of the disclosed therapies). In one example, administration of the disclosed therapies can be used to treat or reduce the undesirable effects of a lymphoma, such as reduce the size of the lymphoma, volume of the lymphoma, rate of growth of the lymphoma, metastasis of the lymphoma, for example a reduction of at least 10%, at least 20%, at least 50%, at least 70%, or at least 90% (as compared to no administration of the disclosed therapies). In one example, administration of disclosed therapies can be used to treat or reduce the undesirable effects of multiple myeloma, such as reduce the number of abnormal plasma cells in the recipient subject, for example a reduction of at least 10%, at least 20%, at least 50%, at least 70%, or at least 90% (as compared to no administration of the disclosed therapies).

For example, the disclosed methods can be used to treat or reduce the undesirable effects of a malignancy that results from a genetic defect in the recipient subject. In one example the disclosed methods reduce the number of cancer cells, the size of a tumor, the volume of a tumor, or the number of metastases, in the recipient subject (such as a subject with a cancer listed above), for example a reduction of at least 10%, at least 20%, at least 50%, at least 70%, or at least 90% (as compared to no administration of the disclosed therapies). In one example, administration of the disclosed therapies can be used to treat or reduce the undesirable effects of a lymphoma, such as reduce the size of the tumor, volume of the tumor, rate of growth of the cancer, metastasis of the cancer, for example a reduction of at least 10%, at least 20%, at least 50%, at least 70%, or at least 90% (as compared to no administration of the disclosed therapies).

For example, the disclosed methods can be used to treat or reduce the undesirable effects of a neurological disease that results from a genetic defect in the recipient subject. In one example the disclosed methods increase neurological function in the recipient subject (such as a subject with a neurological disease listed above), for example an increase of at least 10%, at least 20%, at least 50%, at least 70%, at least 90%, at least 100%, at least 200%, at least 300%, at least 400%, or at least 500% (as compared to no administration of the disclosed therapies).

Example 1

Treatment of Twitcher Mouse Model of Krabbe Disease

This example describes methods used to treat a twitcher mouse model of Krabbe disease using an adeno-associated virus serotype rh.10 vector carrying the GALC gene (AAVrh.10-mGALC) following hematopoietic stem cell transplantation (HSCT) (Rafi et al., Mol Ther. 23(11):1681-90, 2015).

The twitcher mouse is a naturally occurring mutant strain, with a phenotype resulting from the absence of GALC activity due to a nonsense mutation in the GALC gene (W339X). The mice show stunted growth and develop abnormalities including tremors at about 20 days of age and hind leg weakness by 30-35 days of age, followed by wasting and death by about 40 days of age. At this time histopathological defects resembling the human disease (e.g., demyelination and inflammatory changes) are found in the CNS and PNS.

Mice were treated at postnatal day (PND) 10, since at this age they more closely resemble infantile disease in the target clinical population. In addition, this strategy a larger volume of viral particles to be administered, for a total dose of $2 \times 10^{11}$ particle units. Myeloablation by busulfan (30 mg/kg) on PND9 was used instead of myeloablation by irradiation, 1 day prior to BMT and 2 days prior to the AAVrh.10-mGALC injection.

Previous studies demonstrated that twitcher mice treated with intravenous injection of this vector alone (no BMT) on PND10 live an average of 65-75 days (compared to about 40 days in untreated mice), and mice treated with BMT alone (no gene therapy) live an average of 65-75 days, although some live longer.

16 mice have been myelosuppressed using busulfan on PND9, followed by bone marrow transplantation (BMT) 1 day later, and then a single intravenous injection of AAVrh.10-GALC was given 24 hours later. As they were transplanted at different times (because of the availability of affected mice), their ages at this time vary. Other than one mouse that died very young from an unrelated cause, the rest are doing well, with some having lived past 300 days of age (FIG. 2). They are maintaining their weight and exhibiting normal behavior, including strength and balance, until more than 300 days of age.

Figure 3:
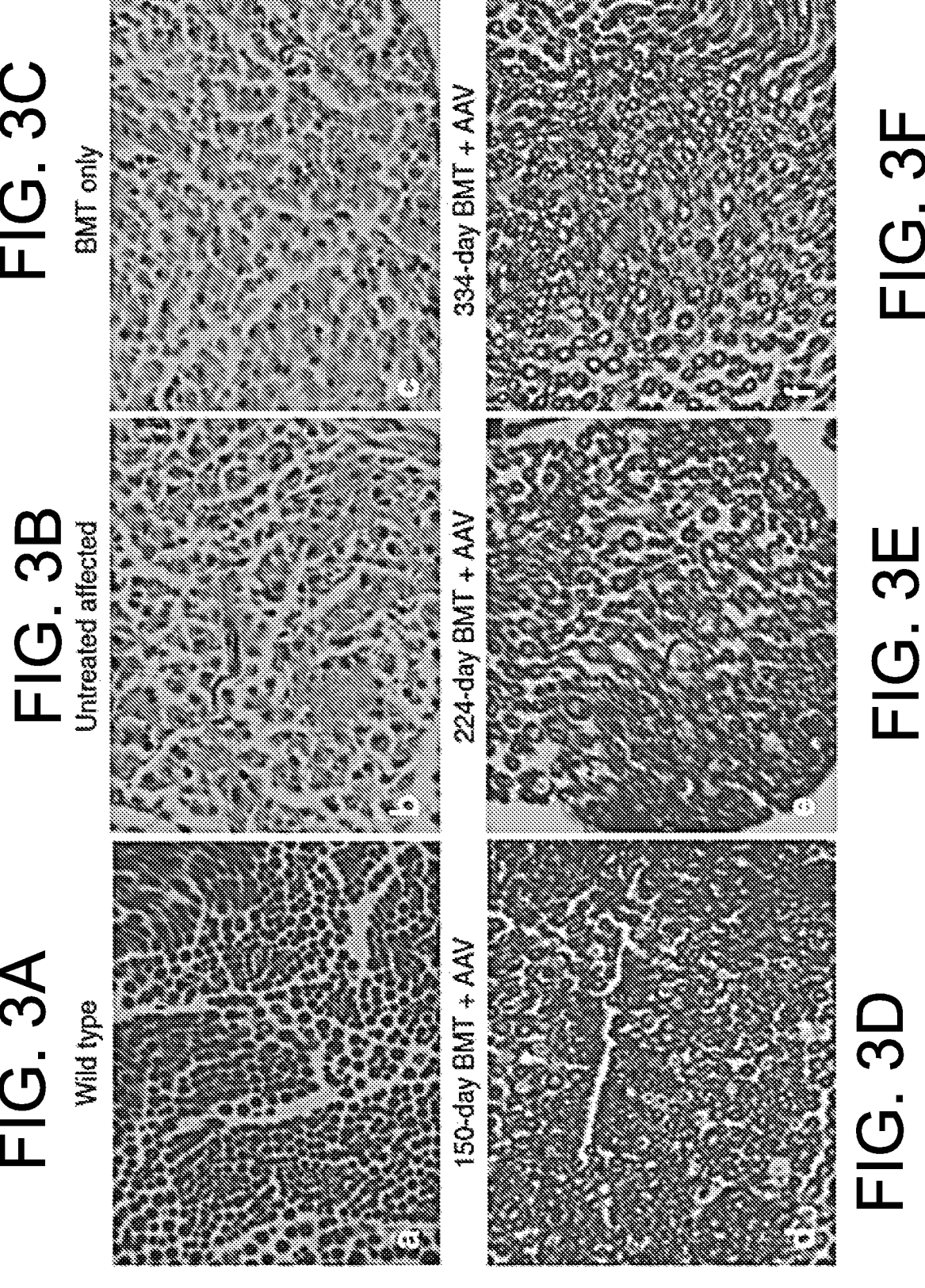
FIGS. 3A-3F. Pathological studies of peripheral nervous system of twitcher mice treated with BMT plus AAV. Cross sections from sciatic nerves of twitcher mice treated with BMT only or BMT+AAV are compared to the similar sections from affected untreated twitcher and wild type mice. All images are from paraffin sections stained with luxol-fast blue/periodic acid Schiff (original magnification× 1,000). The wild-type mouse (a) shows normal myelination, whereas the 42-day-old untreated affected (twitcher) mouse (b) has essentially no myelin and many macrophages. The 98-day-old twitcher mouse treated with BMT only (c) has lost essentially all myelin and is comparable to the untreated twitcher mouse. In contrast, sciatic nerves from mice of different ages treated with combined BMT/AAVrh10 (d-f) have completely normal looking myelin and are comparable to the wild-type mouse. From Rafi et al., *Mol. Ther.* 23:1681-90, 2015.

The tissues from four mice treated with this combination therapy were examined. GALC enzyme activity was normal in the brain, cerebellum, and spinal cord and above normal in the sciatic nerve. Very high GALC activity was measured in the liver, heart, and muscle. Greatly improved myelination in all nervous tissues was seen following combined therapy. Normal myelination in the sciatic nerve is the most dramatic finding, as this tissue is not corrected by other treatment methods (FIG. 3). There was much less astrogliosis in all nervous tissues, and staining for CD68-positive cells (activated macrophages) was reduced to normal in all nervous tissues except the spinal cord, where some CD68-positive cells were seen. This data indicates that BMT followed by a single intravenous injection of AAVrh.10-mGALC provides better outcomes than either treatment alone. It is thought that AAVrh.10 supplies ample GALC activity to the brain, cerebellum, spinal cord, and sciatic nerve, and BMT helps control the inflammation seen in this disease.

Thus, intravenous infusion of AAVrh.10-mGALC shortly after hematopoietic stem cell transplantation (HSCT) rapidly halted disease progression in twitcher mice. This combination treatment provided better outcomes than either treatment alone. AAVrh.10-GALC rapidly supplies GALC activity to the brain, spinal cord, and peripheral nerves, and HSCT controls the inflammation seen in Krabbe disease.

Example 2

Timing of Administration

This example describes methods that can be used to compare the efficacy of intravenous AAVrh.10-GALC infused after HSCT at three time points in the twitcher mouse: postnatal day (PND) 11, 15, and 20.

In previous studies, mice received AAVrh.10-GALC 1 day after HSCT and 2 days after chemotherapy. However, infusing AAVrh.10 this close to HSCT has not been done in humans. Thus, it will be determined whether a similar effect can be achieved if the administration of AAVrh10-GALC a few days later, when donor cell homing and repopulation will have occurred (~14 days post-transplant). Complete hematopoietic repopulation in syngeneic transplanted mice occurs within 10 days after HSCT (Sadelain et al., *J. Immunol.* 144:1729-36, 1990); therefore, the efficacy of HSCT will be performed on PND10 followed by intravenous infusion of AAVrh.10-GALC at PND11, 15, and 20.

Forty-six mice, randomly assigned to four groups, will receive syngeneic HSCT at PND 10, one day after intraperitoneal injection of 30 mg/kg busulfan. $3\text{-}5 \times 10^7$ cells are suspended in 0.2 ml sterile non serum DMEM, and then administered IP. Three of the four groups (each group, n=10) will receive one dose of AAVrh.10-GALC at 1, 5, or 10 days after HSCT (PND 11, 15, 20). The fourth group (n=16 mice) treated with HSCT only will serve as the control. Primary outcome measures will be survival to 150 days and weight at PND60 and PND90 (to assess overall health in the surviving mice). From the sacrificed mice we will collect brain tissues (cortex, cerebellum, brain stem), liver, heart, skeletal muscle, spleen, and sciatic nerve and compare GALC distribution, as assessed by enzymatic activity assay and immunohistochemistry.

Example 3

Dosing of AAVrh10-GALC

This example describes methods that can be used to establish the minimal dosing of intravenous AAVrh.10-GALC following HSCT in twitcher mice for long-term survival.

The minimum effective dose of AAVrh.10-GALC (i.e., smallest dose that results in statistically significant improvement in survival) will be determined. An intravenous AAVrh.10-GALC dose of $4\times10^{13}$ genome copies (gc)/kg will be the maximum dose examined. The lowest dose will be two orders of magnitude lower, $4\times10^{11}$ gc/kg, which also scales well to a human subjects. The middle dose will be $4\times10^{12}$ gc/kg, which corresponds to a total dose for a human newborn of about $2\times10^{13}$ gc. If the maximum tested dose in twitcher mice results in longer survival than the other doses, higher doses can be tested.

As in Example 2, four groups of mice will receive syngeneic HSCT at PND 10, one day after intraperitoneal injection of 30 mg/kg busulfan. At the optimal day determined in Example 2, three of the four groups (each group, n=10) will be treated intravenously with one dose of AAVrh.10-GALC at $4\times10^{13}$, $4\times10^{12}$, or $4\times10^{11}$ gc/kg. The fourth group (n=16 mice) treated with HSCT only will serve as the control. Primary outcome measures will be survival to 150 days and weight at PND60 and PND90.

Example 4

Treatment of Krabbe Disease in Dogs

This example describes methods that can be used to treat a dog model of Krabbe disease using immune ablation chemotherapy, HSCT, and intravenous AAVrh.10-GALC infusion after HSCT, using the optimal timing and minimum effective dose established in mice.

Dogs heterozygous for the GALC mutation has been established at the School of Veterinary Medicine at the University of Pennsylvania. Radiation has traditionally been used as the immune ablation method in Krabbe disease dogs; however, this method does not reflect the conditioning regimen currently used in humans. Chemotherapy-based methods have been tested in dogs, but this will be the first to examine chemotherapy-based conditioning before HSCT in Krabbe disease dogs.

Two dogs will be transplanted using a chemotherapy-based regimen developed for dogs but not previously tested in Krabbe disease dogs. The dogs will receive cyclosporine for 30 days (to mimic the human treatment) and then receive oral hydroxyurea at ~30 mg/kg/day for 2 weeks prior to initiation of the busulfan regimen. On days −3 and −2 prior to HSCT, dogs will receive 5 mg/kg/day busulfan (1 mL busulfan diluted in 9 mL saline) administered intravenously by a syringe pump over a 1-hour period. The primary outcome measure will be survival beyond 24 weeks with normal blood counts, in which case transplantation without irradiation will be deemed successful. All dogs living at 24 weeks will be sacrificed for histopathological studies.

Dogs will be randomly assigned to one of the following groups: untreated (n=2), HSCT only (n=3), or HSCT+ AAVrh.10-GALC (n=3). The dose and timing of AAVrh.10-GALC treatment will be based on results in mice (Examples 2 and 3). The outcomes of treated vs. untreated dogs will be compared at 12 weeks and the outcomes of treatment groups (HSCT only vs. HSCT+AAVrh.10-GALC) compared at 24 weeks.

Primary outcome measures will include results of nerve conduction velocity and brain MRI using diffusion tensor imaging and fractional anisotropy measurements. Exploratory outcomes will include onset of ataxia and tremor. Although survival after transplant will be examined, all dogs still living at 24 weeks will be sacrificed to collect brain tissue (cortex, cerebellum, brain stem), cervical spinal cord, peripheral nerves (sensory, motor, and autonomic), liver, kidney, heart, quadriceps, gonads, spleen, small and large intestine, adrenals, and skin for histopathological studies and assessment of GALC distribution by enzymatic activity assay and immunohistochemistry.

Example 5

Treatment of Krabbe Disease in Rats

This example describes toxicology studies that will be performed in rats. Intravenous AAV will be delivered to immunoablated rats 1 day after UCBT. The new immune system has normal GALC enzyme and would therefore should not react to the GALC enzyme the way naïve patients do.

Toxicology studies will be performed in Fischer 433 rats. Use of Sprague-Dawley rats as bone marrow donors provides a true allogeneic BMT, in contrast to the autologous BMT that has been used in twitcher mice (see Example 1). Using small rodents allows n=5 of each sex per group, and this larger size of rats relative to mice allows easier collection of sufficient blood for complete blood count and serum chemistry tests from one animal at the time of sacrifice. Weaned rats (21 days of age), will be used because of the need for extensive handling for immunosuppression, BMT, and AAV administration.

A summary of the treatment groups is shown in Table 2. An AAVrh.10-hGALC vector intended for humans or rats will be used. Because the human GALC gene will be used in rats, there is a potential of immunogenicity (although they will be immunosuppressed). To minimize aggregation and maximize penetration of blood brain barrier, the vector will be formulated in 380 mM PBS with 5% sorbitol as intended for humans. There are potential complications from BMT alone, including graft-versus-host disease (GVHD). Thus, a negative control group and a group treated with BMT plus vehicle instead of AAVrh.10-hGALC will be examined. In addition, adverse effects of intravenous AAV may be enhanced by BMT; therefore, a group receiving AAV alone will be examined.

TABLE 2

Treatment groups for safety assessment of combined AAVrh.10-hGALC and BMT in rats.

| Group | Animal # | Immuno-suppression and BMT[1] | AAVrh.10-hGALC[2,3] | Time points (days)[3] |
|-------|----------|-------------------------------|---------------------|-----------------------|
| A | 1-30 | + | Vehicle | 7, 30, 180 |
| B | 31-60 | + | $4\times10^{12}$ gc/kg | 7, 30, 180 |

TABLE 2-continued

Treatment groups for safety assessment of
combined AAVrh.10-hGALC and BMT in rats.

| Group | Animal # | Immuno-suppression and BMT[1] | AAVrh.10-hGALC[2,3] | Time points (days)[3] |
|---|---|---|---|---|
| C | 61-90 | + | $4 \times 10^{13}$ gc/kg | 7, 30, 180 |
| D | 91-120 | + | Maximum achievable, ($2 \times 10^{14}$ gc/kg) | 7, 30, 180 |
| E | 121-150 | – | Maximum achievable, ($2 \times 10^{14}$ gc/kg) | 7, 30, 180 |
| F | 151-180 | – | Vehicle | 7, 30, 180 |

[1]Immunosuppression, Busulfan followed by 1 day of mycophenolate mofetil and 4 days of tacrolimus. $1 \times 10^7$ unfractionated mononuclear cells from bone marrow of a Sprague-Dawley donor rat will be infused.
[2]AAV gene transfer. One day after BMT, rats will receive an intravenous injection of the stated dose of AAVrh.10 expressing human GALC cDNA driven by the CMV-enhanced chicken β-actin promoter.
[3]Rats (n = 5 of each sex per time point) are sacrificed by barbiturate treatment, and cardiac puncture is used to collect blood for complete blood count and serum chemistry tests. The rats will be examined for any gross abnormalities, which will be recorded and excised. The following organs will be removed and weighed: liver, kidney, heart, and lungs. Samples of the following organs will be taken for histopathological examination and quantitation of any abnormal findings: adrenal gland, brain (cortex, cerebellum), colon, diaphragm, duodenum, epididymis, esophagus, gross lesions, heart, ileum, kidney, liver, lung/bronchi, >2 lymph nodes, skeletal muscle, sciatic nerve, ovary, pancreas, spinal cord, spleen, testis, and uterus. A blinded evaluation of hematoxylin and eosin-stained sections for each organ is performed. Duplicate samples of the same tissues will be retained and analyzed for vector level by qPCR.

Lot-release criteria for vectors to be used are shown in Table 3. All vectors will be stored in aliquots at ≤–60° C. and thawed on the day they are to be used.

TABLE 3

Lot release criteria for AAVrh.10 hGALC vectors

| | Test/spec | Toxicology grade |
|---|---|---|
| Sterility | No growth observed in 3 test media, 14 days | AppTec |
| Mycoplasma | Not detected | AppTec |
| Endotoxin | LAL (Endosafe) < 10 EU/mL | In house |
| Potency | Infect 293T cells, assay GALC activity in supernatant, record results | In house |
| Genomic structure | Identity of packaged DNA (between ITRs) confirmed by sequencing | In house |
| Purity | SDS-PAGE, showing 3 bands for VP1, VP2, and VP3 at a ratio of 1:1:10 with minimal other bands visible | In house |
| Identity | Western blot using anti-AAVrh.10 antibodies; presence of VP1, VP2, and VP3 bands | In house |
| Appearance | Transparent and colorless | In house |
| pH | Test strip, pH 6.5-7.5 | In house |
| Concentration | qPCR, >2 × $10^{13}$ gc/ml | In house |
| In vitro adventitious virus | 3 cell lines, no cytopathic effect | AppTec |
| Replication-competent AAV | Limiting dilution on 293T cells in presence of adenovirus helper virus, no AAV replication | In house |
| Presence of host cell DNA | qPCR; <100 ng per dose | In house |
| Presence of host cell protein | Record results | In house |
| Empty:full ratio of capsids | Transmission electron microscopy; ≥50% full capsids | In house |
| Residual plasmid DNA | qPCR; ≤100 pg per $10^9$ AAV particles | In house |

A target dose of $4 \times 10^{13}$ gc/kg AAVrh.10-mGALC by intravenous injection will be used. Twitcher mice, received $2 \times 10^{11}$ gc, which equates to approximately $4 \times 10^{13}$ gc/kg body weight. For a 5-kg infant newly diagnosed with Krabbe disease, this translates to $2 \times 10^{14}$ gc total.

Based on a target human dose of $4 \times 10^{13}$ gc/kg, rats will be assessed at: A), target dose; B), 0.1×target dose and C), maximum achievable dose. If the injection volume is 200 μl and the high grade vector can be provided at $2 \times 10^{13}$ gc/ml, and that the rats are 40 g, then the maximum achievable dose is $2 \times 10^{14}$ gc/kg.

Rats will be sacrificed at 7, 30, and 180 days. At 7 days after infusion, any active infection resulting from AAVrh.10-hGALC infusion may be evident; at 30 days the immune system will be fully reconstituted and any anti-AAV or anti-transgene reaction will be apparent; and at 180 days long-term effects will be evident. This longer time point relates to the possibility of liver carcinoma following intravenous AAV injection into newborn mice.

Example 6

Treatment of Krabbe Disease in Humans

This example describes an open label phase I/IIa study to evaluate safety and clinical outcomes of combination treatment with intravenous gene therapy (AAVrh.10-hGALC) plus unrelated UCBT in infants with infantile Krabbe disease. Disease-related outcome parameters include results of a battery of standardized neurodevelopmental tests (including cognitive and motor skills), brain MRI, nerve conduction studies, and a lumbar puncture, which will be performed at baseline, 100 days after treatment, and every 3 months thereafter for a total of 5 visits. This interval is necessary since this period represents a time of rapid brain growth in a baby. Annual follow ups for at least 5 years after the end of the formal study period will be performed.

The sample size (8 patients) has been chosen according to logistical and practical considerations based on the rarity of the disease. Although the sample size is small, this is typical for rare diseases. Fortunately the effect size that is of clinical interest is large compared to the between-subject variability. Previous studies of treatments for patients with Krabbe disease that were diagnosed early suggest a population effect size of 1.5-2.0 standard deviations. Although 4 subjects per group is a small sample, the study will have good power (80%) to detect differences of 1.25 standard deviations between the Krabbe disease group and control children with typical development. Differences >1.25 standard deviations are expected between successful treatment and natural disease progression. However, to better estimate the between-subject variability the study will collect longitudinal data, which will be analyzed with bootstrap analysis.

Eight patients will be divided into 2 dose cohorts (Table 4). Four patients will undergo AAVrh.10-hGALC/UCBT with the lowest vector dose, followed by 4 additional patients in a higher-dose cohorts. The first group will be given the standard reduced-intensity conditioning chemotherapy regimen and unrelated UCBT (as described below). On the day following UCBT, eligible babies will receive one intravenous injection of AAVrh.10 expressing human GALC cDNA and remain in the hospital until they are transfusion-independent, engrafted, and deemed stable. Based on patients who do not receive AAVrh.10-hGALC, this will take at least 4 weeks; therefore, subjects will be monitored daily in the transplant unit during the immediate post-gene transfer period, when vector-related adverse events are most likely. At approximately day 30-60, patients will be discharged 1 and followed weekly. At 3-month intervals thereafter, the subjects will be subjected to comprehensive evaluations (Table 5). The first subject in Group A will be followed for 3 months before the subsequent subjects are enrolled.

TABLE 4

| | | |
|---|---|---|
| Patient groups for combined intravenous AAVrh.10-hGALC and UCBT | | |
| Cohort | Number of patients | Dose |
| A | 4 | 0.25 × target dose |
| B | 4 | Target dose of 4 × $10^{13}$ gc/kg (pending pre-clinical safety study) |

There are no precedents for the use of intravenous AAV-mediated gene therapy in severely immunosuppressed subjects; therefore, this phase I/IIa study will focus primarily on safety. As a result, the study will be performed with no simultaneous control group. However, known infantile Krabbe disease patients who have been prospectively assessed using a standard protocol with the same parameters, shows the expected course of the disease in both untreated patients (n=79) and patients treated with UCBT (n=54). These existing data are sufficient to determine the expected time-dependent changes in outcome parameters, as well as standard deviations of such measures. This allows a formal statistical assessment of disease progression in those patients treated with the combination therapy.

Eight patients will be enrolled regardless of gender, race, or ethnicity. Inclusion criteria are as follows:

1. Confirmed diagnosis of infantile Krabbe disease, galactocerebroside ß-galactosidase (GALC) activity<0.20 nmol/h/mg protein in leukocytes, and two pathogenic GALC mutations after the baseline visit.
2. Age at the time of screening: 1 day to 12 months.
3. Abnormality in neuroimaging, nerve conduction studies, or brainstem auditory evoked potentials
4. Eligible for unrelated UCBT.
5. Parent(s) and/or legal guardian able to comply with the clinical protocol.

Exclusion criteria are as follows:

1. History of previous HSCT.
2. Presence of known clinically significant cardiovascular, hepatic, pulmonary, or renal disease or other medical condition.

3. Presence of major congenital anomaly.
4. Abnormal blood tests at screening, including signs of active infection or history of active cytomegalovirus, Epstein-Barr virus, herpesvirus, or adenovirus.
5. Any other medical condition, serious intercurrent illness, or extenuating circumstance that, in the opinion of the PI, would preclude participation in the study.
6. Use of any investigational product within 30 days prior to study enrollment or currently enrolled in another study that involves clinical investigations.
7. Patient's parent(s) and/or legal guardian are unable to understand the nature, scope, and possible consequences of the study.
8. Patient is unable to comply with the protocol (i.e., unable to return for follow-up evaluations or otherwise unlikely to complete the study), as determined by the PI.

Immunosuppression and Umbilical Cord Blood Transplantation

Umbilical cord blood transplantation from a 4-6 of 6 HLA-matched donor is considered standard of care for presymptomatic or minimally symptomatic Krabbe disease. The patients will receive a reduced-toxicity conditioning regimen, which decreases transplant-related morbidity and mortality. The backbone of this chemotherapy regimen is myeloablative doses of busulfan, which has been used as standard of care for Krabbe disease and many other non-malignant disorders. Moreover, busulfan has been the chemotherapy agent of choice in most gene therapy trials. Patients will receive alemtuzumab (0.5 mg/kg), hydroxyurea (30 mg/kg/day), fludarabine (1 mg/kg/day×4 days), busulfan (about 4 mg/kg/day×3 days), with tacrolimus and mycophenolate mofetil (MMF) for GVHD prophylaxis.

Busulfan will be administered over 3 days at ~12 mg/kg with therapeutic drug monitoring and dose adjustment to achieve a targeted steady-state concentration of 850 mg/dl. Lower busulfan exposures may result in graft failure, especially with cord blood grafts, where the infused CD34+ progenitor cell dose and total nucleated cell dose are ~1 log lower than bone marrow grafts.

Patients will be given immunosuppressive medications, which will include intravenous tacrolimus (starting at ~0.05 mg/kg/day) and intravenous MMF starting 2 days prior to transplant. MMF (initiated at 45 mg/kg/day, split into 3 doses) will be given for the first 28 days as our standard regimen, and then decreased rapidly in the absence of grade 2-4 GVHD. Conversion to oral dosing will be done after 3-4 weeks, as tolerated. Tacrolimus (or its substitute cyclosporine A) will be continued for the first 3-4 months after transplant, and the patient will then be weaned off over 2-3 months in the absence of GVHD. Safety monitoring of the immunosuppressant therapy will include blood tests performed daily for the first 3-4 weeks and thereafter as clinically indicated until tacrolimus is discontinued. Safety blood tests will include: complete blood count/differential/reticulocytes, comprehensive metabolic panel, and tacrolimus levels. The patients will continue to be monitored for adverse events as per the standard transplant protocol.

TABLE 5

| | Evaluations performed prior to transplant | 0 to 6 mo | >6 mo |
|---|---|---|---|
| History and Examination | Medical history, prior treatment toxicities, performance status (Lansky or Karnosfky), immunization history, height, weight, BMI, vital signs Ages 10-18: Tanner staging | X | X |
| Basic Labs Blood | CBC + Diff, PT/PTT, fibrinogen, ABO/Rh, basic metabolic panel, liver function tests, renal glomelurar function | X | X |
| | Menstruating females only; Serum beta-hCG | | |
| Infectious Disease Blood Labs | Antibody titers: HBsAg, HBc, HCV, HIV/HCV/ HBV NAT IDS, WNV NAT IDS, HIV I/II, HTLV I/II, CMV, *T. cruzi*, syphilis screen, EBV, VZV, HSV, Toxoplasma, ADV by PCR | X | X |
| | EBV PCR, VZV PCR, HSV PCR, CMV PCR | X | X (if receiving IVIG) |
| Infectious Disease Respiratory Labs (NP Swab) | Respiratory viral panel | X | X |
| Infectious Disease Stool Labs | ADV by PCR, Norovirus by PCR, *C. diff* by PCR | | X |
| | PID patients only: Ova & Parasites | X | X |
| Molecular testing Blood | DNA for chimerism (e.g., STR Assay), HLA typing, Panel Reactive Antibody (PRA) | X | X |
| Organ studies | Echocardiogram, EKG, pulmonary function tests | X | X |
| Imaging | Chest X-Ray; CT Brain, sinuses, chest abdomen, pelvis EXCEPT Patients with radiation-sensitive chromosomal breakage syndromes (e.g., Dyskeratosis congenita) WILL HAVE: MRI of the brain, sinuses, chest, abdomen, pelvis | X | X |
| Drug levels Blood | Alemtuzumab level - Prior to administration | | X |
| | Alemtuzumab level - Day 0 | | X |
| Research Studies Blood | Immune Reconstitution Sample: 2 mL blood in a green top tube, not to exceed 1 mL/kg | X | X |
| | Additional research immune studies (immune recovery, specific viral immunity) Sample: 2 mL blood in a green top tube (may share with above) | X | X |
| Neurodevelopmental evaluation | Behavioral audiometry, Brainstem auditory evoked responses, visual evoked potentials, Mullen Scales of Early Learning, GMFM, ophthalmology exam CSF Protein, Spine MRI, nerve conduction velocity, EEG, mutation analysis, GALC enzyme level | X | X |

Following transplant, the following will be evaluated:

1. CBC— thrice weekly from day 0 through neutrophil engraftment, then twice weekly through day 28 and weekly through week 12. Reticulocyte counts will be performed once weekly along with a CBC.

2. Basic metabolic panel and liver function testing—twice weekly through day 28, then weekly through week 12.

3. Adenovirus-blood PCR twice weekly following alemtuzumab until Day +50 or posttransplant discharge, whichever is earlier, then weekly through Day 100.

4. CMV: those with no prior viral exposure—blood PCR weekly through day 100; those with suspected/proven CMV exposure: blood PCR twice weekly following alemtuzumab until Day +50 or post-transplant discharge, whichever is earlier; then weekly through Day 100.

5. EBV PCR—every two weeks following alemtuzumab through day 100.

6. GVHD grading—weekly through day 100

Additional details are provided in Table 6.

TABLE 6

| | | | | | | | | | | | | wk12 3 mo 100 days | 6 mo 180 days | 9 mo 270 days | 12 mo 365 days | 24 mo 730 days |
|---|---|---|---|---|---|---|---|---|---|---|---|---|---|---|---|---|
| | | | | wk4 1 mo | | | | wk8 2 mo | | | | | | | | |
| | wk1 | wk2 | wk3 | | wk5 | wk6 | wk7 | | wk9 | wk10 | wk11 | | | | | |
| Physical examination[1] | | | | X | | | | X | | | | X | X | X | X | X |
| GVHD grading | X | X | X | X | X | X | X | X | X | X | X | X | X | X | X | X |
| CBC, Reticulocyte Count[2] | 2-3× | 2-3× | 2-3× | 2-3× | X | X | X | X | X | X | X | X | X | X | X | X |

TABLE 6-continued

Post-Transplant procedures

| | wk1 | wk2 | wk3 | wk4 1 mo | wk5 | wk6 | wk7 | wk8 2 mo | wk9 | wk10 | wk11 | wk12 3 mo 100 days | 6 mo 180 days | 9 mo 270 days | 12 mo 365 days | 24 mo 730 days |
|---|---|---|---|---|---|---|---|---|---|---|---|---|---|---|---|---|
| BMP, LFT, Total Protein, Albumin[2] | 2× | 2× | 2× | 2× | X | X | X | X | X | X | X | X | X | X | X | X |
| Thyroid function testing | | | | | | | | | | | | | X | X | | X | X |
| Gonadal function[3] | | | | | | | | | | | | | | | | X | X |
| CMV, Adenovirus by PCR (see text for frequency) | X | X | X | X | X | X | X | X | X | X | X | X | | | | |
| EBV by PCR | | X | | X | | X | | X | | X | | X | | | | |
| Chimerism studies[4] | | | | X | | | | X | | | | X | X | X | X | X |
| Immune reconstitution studies | | | | X | | | | X | | | | X | X | X | X | X |
| Humoral immune studies | | | | X | | | | X | | | | X | X | X | X | X |
| Imaging studies[5] | | | | | | | | | | | | X (optional) | X | X (if d180 is abnormal) | X | X |
| Organ toxicity[6] | | | | X | | | | X | | | | X | X | | X | X |

[1]Including height, weight, OFC (patients <2 yr)
[2]CBC with differential, basic metabolic panel, liver function testing with total protein and albumin. Reticulocyte counts will be performed once weekly along with a CBC.
[3]FSH, LH, estradiol, testosterone (age and sex specific)
[4]Total chimerism as well as myeloid and lymphoid fractions; via RFLP. Initial assessment at the time of engraftment or by day 30.
[5]Chest x-ray; echocardiogram, EKG, pulmonary function testing. Disease-specific Day 100 imaging studies are optional; consult neurodevelopmental disability or attending service for required studies. Obtain studies on day 270 if day 180 testing is abnormal, or if clinically indicated.
[6]NCI CTCAE version 3.0

Venous Access—prolonged central venous access will be necessary for all patients for hydration, chemotherapy, total parenteral nutrition, transfusion of blood products, antibiotics, blood lab draws, etc. Two double lumen catheters (e.g., Broviac) are preferred but a triple lumen catheter may be acceptable.

Patients with transfusion dependent anemia:

Transfusion—patients will be transfused a minimum of 4 weeks pre-transplant to a goal hemoglobin>12 g/dL for patients with thalassemia and a goal of 9-12 g/dL for patients with sickle cell disease.

Chelation—patients on chronic transfusion therapy and with evidence of iron overload (ferritin>1000 ng/mL) will receive chelation a minimum of 4 weeks pre-transplant with either desferral 20-100 mg/kg/day SC or IV continuous infusion over 12 hours nightly or oral deferasirox (Exjade).

Transplant Preparative Regimen

Hydroxyurea will be given orally at a single daily dose of 30 mg/kg, rounded to the nearest pill size. The use of PRN G-CSF at 5 mcg/kg (max 300 mcg) is encouraged for ANC of <750 cells. If, despite the use of G-CSF, ANC falls to <500 cells/µL hydroxyurea will be held.

Alemtuzumab will be given IV per current institutional guidelines. A single dose of alemtuzumab will be given at 0.5 mg/kg/dose on Day −10 or −9. Appropriate premedications will be given according to institutional guidelines If the patient has a fever>38.5 C during or after alemtuzumab infusion, blood cultures will be drawn and antibiotic coverage will be added.

Fludarabine will be given IV at a dose of 30 mg/m2/dose (or 1 mg/kg/dose, whichever is lower) over 1 hour daily×5 doses on days −9 to −5.

Medication Administration

Adjusted ideal body weight (AIBW) will be used for obese patients with weight>125% of their ideal body weight (IBW). IBW Calculation in kilograms (from CHP Pediatric Drug Therapy Handbook): Children (1-2 years): <60 inches: IBW=(height$^2$ [in cm]×1.65)/1000; >60 inches: Males: IBW=39+(2.27×height in inches over 5 feet), Females: IBW=42.2+(2.27×height in inches over 5 feet). Adjusted IBW (AIBW) Calculation from actual body weight (ABW): AIBW=IBW+[(0.25)×(ABW−IBW)]

Umbilical Cord Blood Selection and Infusion

The best available unit will be selected based on HLA (minimum 4 of 6 HLA match with allele level HLA-DRB1 typing), total nucleated cell dose (minimum 3.0×10$^7$/kg AIBW), CD34+ progenitor dose (minimum 1.5×10$^5$/kg AIBW) and other factors impacting on potency (such as enzyme activity for patients with inherited enzyme deficiencies). UCB unit will be thawed and infused with or without dilution. No more than 5% of the thawed cord blood or living unrelated donor marrow graft will be refrozen on Day 0, to be infused at a later date. All products will be irradiated to decrease the risk of graft-versus-host disease. Additionally, all products will be CMV-safe (leukocytes that could contain CMV have been removed) and will be filtered to deplete red blood cells and leukocytes to decrease the incidence of HLA antibody formation. Patients will receive red blood cell and platelet transfusions.

Granulocyte colony-stimulating factor (G-CSF), 5 mcg/kg/dose daily IV or SC will be begun on day +1 and continued until ANC is ≥2,000. Thereafter, dose adjustment discontinuation of G-CSF will be determined based upon individual patient conditions. Intravenous nutrition with total parenteral nutrition (TPN) and intralipids will be initiated when oral intake significantly decreases and tapered/discontinued once oral intake improves, at the discretion of the physician. Liver function, protein/albumin, and triglyceride levels will be monitored closely during IV nutrition.

GVHD

For prophylaxis, patients will receive tacrolimus and mycophenolic acid (MMF/cellcept) for GVHD prophylaxis. Continuous infusion or Q12h dosing of IV tacrolimus will begin on day −2 and can be converted to oral once the patient is tolerating PO intake. Tacrolimus levels on continuous infusion will be monitored at least three times weekly with goal of 12-15 ng/ml steady state level with LC/MS method. In cases of Q12h intermittent dosing the target through levels will be between 8-10 ng/ml. Mycophenolic acid (15 mg/kg/dose) will be given IV every 8 hours over 2 hours beginning day −2 until day 28 with wean over the next week in the absence of grade 2-4 acute GVHD. Earlier wean of MMF or lower target range of Tacrolimus may occur if there is concern for toxicity, or active viral infections and/or delayed lymphocyte recovery.

Diagnosis and treatment of acute GVHD will be based on current institutional guidelines that reflects current BMT CTN guidelines. Diagnosis of chronic GVHD will be based upon clinical and/or histopathological data and current standard diagnostic criteria.

Infections

Prior to conditioning, all patients should be free of any cutaneous or mucosal infections. CT scan of the brain, sinuses, chest, abdomen, and pelvis will be obtained pretransplant to screen for occult infection unless contraindicated, in which case alternative imaging will be performed. All patients will receive chlorhexidine gluconate baths (hibiclens). Patients will be monitored for constipation, particularly if receiving narcotics, and stool softeners will be begun as indicated. All patients will be housed in a private room with HEPA filtration.

Patients (unless allergic to sulfa drugs) will receive *Pneumocystis* (*carinii*) *jiroveci* pneumonia (PCP) prophylaxis with sulfamethoxazole-trimethoprim (Bactrim); this will start during conditioning. Pentamidine or an appropriate substitute begin day +28 until immune reconstitution occurs (CD4+ T cells>300 cells/mm3 in the absence of systemic steroids) unless clinically contraindicated. Pentamidine may be changed to oral Bactrim or alternative oral PCP prophylaxis.

Patients with positive HSV and/or VZV serology due to infection or exposure and/or a history of chicken pox infection will receive acyclovir IV. When tolerating PO intake, the acyclovir may change to oral. If the patient is receiving ganciclovir, foscarnet or cidofovir, it is not necessary to also give acyclovir unless a combination approach is appropriate. Prophylaxis will be continued until CD4+ T cells>250 cells/mm3 in the absence of systemic steroids and clinically significant levels of other systemic immunosuppressive agents. It is not expected that prophylaxis will be stopped prior to 6 months posttransplant unless adverse effects of these drugs warrant discontinuation.

HSVNZV prophylaxis is not required for the following patients provided there is no clinical evidence of prior HSVNZV infection or exposure, for example positive serology is due to the use of IVIG with negative HSVNZV PCR; positive serology due to maternal transfer of IgG in patients less than 6 months of age with negative HSVNZV PCR; or positive serology due to immunization.

Patients with who have HSV/VZV viremia at the time of enrollment or who develop viremia prior to transplant can be treated.

Patients with positive CMV serology or detectable virus in saliva, urine or other sites but no detectable viremia will receive ganciclovir or other CMV-specific therapy at maintenance dosing (typically 5 mg/kg IV daily) from day −12 through day −2 during conditioning, followed by acyclovir 500 mg/m² IV every 8 hours starting day +1 through day +100 with dose adjustment for renal insufficiency. Daily foscarnet (90 mg/kg/day) may be substituted. Those with CMV viremia pre-transplant can receive appropriate anti-CMV therapy before and during cord blood infusion. CMV prophylaxis is not required for the following patients provided there is no clinical evidence of prior CMV infection or exposure, for example: positive serology is due to the use of IVIG with negative CMV PCR or positive serology due to maternal transfer of IgG in patients less than 6 months of age with negative CMV blood PCR or other diagnostic studies performed from saliva or urine.

Patients will receive fungal prophylaxis from Day +1 on a clinically-appropriate dose and schedule. Prophylaxis will initially include caspofungin followed by transition to voriconazole prior to discharge to the outpatient setting with targeting of therapeutic levels.

Patients will receive IVIG as general immunoprophylaxis according to the following schedule:

Day −15 to +55 post-transplant: every 2 weeks

After day +55 post-transplant: Monitor serum IgG levels q2-3 weeks and supplement with IVIG to keep IgG over 750 mg/dL. IgG supplementation will be continued until IgA levels are normal and CD4 T-cell count is over 200/uL.

Patients will receive bacterial prophylaxis with levofloxacin or an appropriate substitute on a clinically-appropriate dose and schedule starting at the discretion of the physician and continuing until engraftment. This will be held at the initiation of broad-spectrum antibiotics in the setting of neutropenic fever.

Patients will be monitored weekly with CMV PCR starting after alemtuzumab and additionally as clinically indicated. Treatment will be initiated in patients with confirmed positive quantitative PCR of any value and/or documented CMV disease. First line therapy will consist of ganciclovir 5 mg/kg/dose IV every 12 hours for 14 days or until CMV PCR is negative or declined to an acceptable level OR the patient's clinical symptoms have resolved, whichever is longer. Maintenance therapy will consist of ganciclovir 5 mg/kg/dose IV daily for 14 days or longer if the patient remains significantly immunosuppressed. Ganciclovir resistance and second line therapy should be considered in patients without clinical improvement after 10-14 days or if PCR titers remain high or increase. Patients should be monitored closely for side effects of myelosuppression and renal dysfunction. Foscarnet or cidofovir may be used prior to engraftment or if clinically indicated.

Patients with new fever (defined as temperature≥38.5° C.×1 or ≥38° C.×2 [taken within 2 hours]) should have a thorough physical examination and blood cultures obtained from all central catheter ports. Additional tests are as clinically indicated but may include chest x-ray or other imaging studies, urine culture, throat or oral culture, viral studies (nasopharyngeal swab), and molecular studies (CMV, adenovirus, BK virus, etc). Blood cultures will be repeated every 24 hours with continued fever or more frequently if clinical change. Empiric broad-spectrum antibiotics will be begun immediately after cultures are obtained. Firstline antibiotics will include piperacillin-tazobactam 75 mg/kg/dose (as piperacillin, 3000 mg max dose) IV every 6 hours and vancomycin 15 mg/kg/dose IV every 6-8 hours. Vancomycin trough levels will be monitored frequently with goal of 8-12 mg/L. Appropriate substitutions may be made for patients with allergies to penicillin or vancomycin. Antibiotics will be adjusted based upon clinical response and identification of bacterial pathogens. Empiric antifungal therapy (including mold coverage) will be considered in patients who remain febrile for greater than 3 days. Antibiotics will be continued until resolution of fever and ANC>500 for minimum of 3 days.

Prevention and Management of VOD

Patients will receive low dose heparin for prophylaxis of veno-occlusive disease (VOD). This will be given as a continuous infusion of 100 units/kg/24 hours from day −9 through day +28 or until discharge. Ursodiol will be administered according to close to baseline as possible VOD will be suspected in patients with hyperbilirubinemia, painful hepatomegaly, ascites, fluid retention. General treatment measures will include close monitoring and correction of fluid imbalance. Loop diuretics at appropriate dose are encouraged Q6-12 h as needed. Severe VOD may be treated with defibrotide.

Evaluation of engraftment and management of graft failure: Definitions (per IBMTR Manual for Clinical Research Professionals, 2003): Neutrophil Engraftment—≥0.5×103/µL neutrophils for three consecutive days tested on different days; Platelet engraftment—platelet count of ≥20,000/µL without platelet transfusion in the previous 7 days; Donor cell engraftment—≥50% donor cells on day +28; Graft Failure—primary failure is defined as lack of neutrophil engraftment (as per above) by day +42 or <10% donor cells in peripheral blood or bone marrow by day +100 on two studies a minimum of 1 week apart. Secondary failure is defined as loss of engraftment after engraftment was previously achieved (according to above criteria).

In patients without evidence of neutrophil engraftment by approximately day +41-44, a bone marrow aspirate and biopsy will be performed to assess chimerism. General evaluation of graft failure will include bone marrow aspirate and biopsy for chimerism, cytogenetics, etc.; microbial studies (marrow and blood) including CMV, EBV, parvovirus, and HHV-6 in addition to other studies if indicated; and peripheral blood for chimerism.

Initial treatment of graft failure/rejection will include support with growth factors and discontinuation of myelo-suppressive medications. A subsequent transplant will be considered in patients with no evidence of donor engraftment or with significant consequences related to cytopenias. Infusion of the reserved donor UCB aliquot may be appropriate.

Vector Administration

The AAVrh.10-hGALC dose will depend on results of animal efficacy and safety studies described above. Scale up from mouse to human will be based on the same genome copies per kilogram body weight (gc/kg). A maximum dose of about $4 \times 10^{13}$ gc/kg, will be given 1 day after UCBT. Two dose cohorts, each with n=4 subjects, starting at 0.25×this target dose, followed by the target dose, will be used.

Clinical-grade vector will be manufactured in a GMP-compliant clean room facility and undergo lot-release testing as described in Table 3. The vector will be monitored to ensure it remains stable over the duration of the clinical study (e.g., by assaying for GALC enzyme activity.

The vector will be administered as a push (1 ml/minute) of the required dose in buffered isotonic saline through the central line that is present to manage the UCBT. This will likely be a 10 ml infusion.

Follow-Up

Individual patient evaluations will be performed as shown in Table 7. Additional patient evaluations will occur at approximately 3, 6, 9, and 12 months after the baseline visit.

TABLE 7

Schedule of disease-related procedures.

| Procedure | Visit 1 | Dosing visit[1] | Visit 2 90 days | Visit 3 182 days | Visit 4 273 days | Visit 5 365 days |
|---|---|---|---|---|---|---|
| PI/informed consent | • | | | | | |
| Initials and date of birth | • | | | | | |
| Demographic information | • | | | | | |
| Medical history/review of systems | • | • | • | • | • | • |
| Inclusion/exclusion criteria | • | | | | | |
| Family history (first-degree relatives) | • | | | | | |
| Past clinical investigations | • | | | | | |
| Medications | • | • | • | • | • | • |
| Physical and neurological examination | • | • | • | • | • | • |
| Vital signs | • | • | • | • | • | • |
| Brain MRI | • | | • | • | • | • |
| Spinal tap/cerebrospinal protein and exploratory biomarkers | • | | • | • | • | • |
| Nerve conduction velocity | • | | • | • | • | • |
| Vision and hearing examinations | • | | • | • | • | • |
| Weight, height, and head circumference | • | | • | • | • | • |
| Genotyping and enzyme testing | • | | | | | |
| Mullen Scales of Early Learning | • | | • | • | • | • |
| Blood drawn for immune/infection studies | • | • | • | • | • | • |
| Peabody Developmental Motor Scale | • | | • | • | • | • |
| Clinical chemistry (blood) | • | • | • | • | • | • |
| GALC activity (blood and cerebrospinal fluid) | • | • | • | • | • | • |
| Anti-AAV antibodies | • | • | • | • | • | • |
| Anti-AAV enzyme-linked immunospot (ELISPOT) | • | | • | • | • | • |
| Shedding analysis of blood, urine, stool, and saliva by PCR | • | • | | | | |

[1]Following dosing of the AAVrh. 10 vector, collections/evaluations will be conducted at 1, 2, 4, and 8 weeks. Additional blood will be drawn to monitor immunosuppression twice weekly for 2 weeks, once weekly for an additional 2 weeks, and if stable and therapeutic, monthly for the next 4 months.

Visit 1—Baseline Evaluation (PRE-UCBT)

The following data is be collected for all patients at baseline:

1. Patient's initials, date of birth, and unique patient ID number.
2. Demographic information.
3. Significant medical history including previous diagnoses, illnesses, medications, procedures, and surgeries.
4. The results of the following clinical investigations, if previously performed: cerebral MRI, nerve conduction studies, and genetic and/or biochemical testing for diagnosis of Krabbe disease. Baseline tests are valid if performed within 3 months of the parent/legal guardian signing informed consent to enter the study.
5. The following examinations will be performed at the baseline visit: cerebral MRI, spinal tap, nerve conduction studies, and vision and hearing examinations.

6. A list of all current medications and frequency of administration.

7. Physical and neurological exam including vital signs (blood pressure, pulse, height, weight, and head circumference).

8. Parent(s) and/or legal guardian will be asked about the patients' family history (first-degree relatives) to ascertain whether any other family members have been diagnosed with Krabbe disease or have clinical signs and symptoms of the disease (but have not been diagnosed).

9. Results of the Mullen Scales of Early Learning and Peabody Developmental Motor Scales.

10. Baseline cerebrospinal fluid (CSF) collection for protein and white blood cell counts as well as GALC activity. The remainder will be archived for future biomarker assessments.

11. Baseline blood collection for clinical chemistry and measurement of anti-AAV antibodies and GALC activity.

12. Baseline blood collection to measure T cell responses against AAVrh.10 and GALC.

13. Baseline collection of samples for vector shedding analysis (blood, stool, urine, and saliva).

The neurodevelopmental evaluation will be performed on day 1. Medical/diagnostic testing will be performed on day 2.

Day 1. Neurodevelopmental evaluation
  1. Medical history and review of concomitant illnesses
  2. List of all current medications and frequency of administration
  3. Hearing examination by an audiologist.
  4. Physical and neurological exam including vital signs (blood pressure, pulse, height, weight, and head circumference)
  5. Administration of the Mullen Scales of Early Learning and Peabody Developmental Motor Scales Day 2 Medical and diagnostic tests
  1. Cerebral MRI
  2. Spinal tap
  3. Nerve conduction velocity studies
  4. Blood draws
  5. Urine, stool, and saliva collection Day 3. UCBT evaluation and preparation for UCBT. Vector will be injected at day +1 relative to UCBT.

At week 1, 2, 4, and 8 following vector administration, sample collections will be carried out as follows:
  1. Blood collection for clinical chemistry, anti-AAV neutralizing antibody detection, vector shedding analysis, and GALC activity
  2. Collection of urine, stool and saliva for vector shedding analysis Visit 2 (90±5 Days Post-UCBT and AAVrh.10-hGALC)
The visit will occur over 2 days and will include:
Day 1. Neurodevelopmental evaluation
  1. Interim medical history and review of concomitant illnesses
  2. List of all current medications and frequency of administration since the last visit
  3. Vision and hearing examination (by an audiologist)
  4. Physical and neurological exam including vital signs (blood pressure, pulse, height, weight, and head circumference)
  5. Administration of the Mullen Scales of Early Learning and Peabody Developmental Motor Scales Day 2. Medical and diagnostic tests
  1. Cerebral MRI
  2. Spinal tap
  3. Nerve conduction studies
  4. Clinical chemistry assays using blood samples
  5. Blood collection for anti-AAV and anti-GALC T cell response using ELISPOT Visit 3 (180 Days±1 Month)
The visit will occur over 2 days and will include:
Day 1. Neurodevelopmental evaluation
  1. Interim medical history and review of concomitant illness
  2. List of all current medication and frequency of administration since the last visit
  3. Vision and hearing examination (by an audiologist)
  4. Physical and neurological exam including vital signs (blood pressure, pulse, height, weight, and head circumference)
  5. Administration of the Mullen Scales of Early Learning and Peabody Developmental Motor Scales Day 2. Medical and diagnostic tests
  1. Cerebral MRI
  2. Spinal tap
  3. Nerve conduction studies
  4. Clinical chemistry assays using blood samples
  5. Blood collection for anti-AAV and anti-GALC T cell response by ELISPOT Visit 4 (270 Days±1 Month)
This visit will occur over 2 days and will include:
Day 1. Neurodevelopmental evaluation
  1. Interim medical history and review of concomitant illness
  2. List of all current medication and frequency of administration since the last visit
  3. Vision and hearing examination (by an audiologist)
  4. Physical and neurological exam including vital signs (blood pressure, pulse, height, weight, and head circumference)
  5. Administration of the Mullen Scales of Early Learning and Peabody Developmental Motor Scales Day 2. Medical and Diagnostic Tests
  1. Cerebral MRI
  2. Spinal tap
  3. Nerve conduction studies
  4. Clinical chemistry assays using blood samples
  5. Blood collection for anti-AAV and anti-GALC T cell response by ELISPOT 5.5.5 Visit 5 (360 Days±1 Month)
The visit will occur over 2 days and will include:
Day 1. Neurodevelopmental evaluation
  1. Interim medical history and review of concomitant illness
  2. List of all current medication and frequency of administration since the last visit
  3. Vision and hearing examination (by an audiologist)
  4. Physical and neurological exam including vital signs (blood pressure, pulse, height, weight, and head circumference)
  5. Administration of the Mullen Scales of Early Learning and Peabody Developmental Motor Scales Day 2. Medical and diagnostic tests
  1. Cerebral MRI
  2. Spinal tap
  3. Nerve conduction studies
  4. Clinical chemistry assays using blood samples
  5. Blood collection for anti-AAV and anti-GALC T cell response by ELISPOT Details of Assessment Methods Physical and neurological examination. A complete physical examination (including evaluation of general appearance, skin, head, eyes, ears, nose, throat, lymph nodes, heart, lungs, abdomen, extremities/joints, and hips) will be performed once during the baseline phase and at the times specified in Table 7. Height or length (cm, supine on a standard measuring board), weight (kg, without shoes or diaper, if wet, and wearing lightest possible clothing), and head circumference (cm, standard occipital frontal) will be measured. These will be compared against natural history data to evaluate potential adverse effects and treatment efficacy.

The extended neurological examination will include evaluation of muscle tone and reflexes and neurodevelopmental function.

Vital signs. Systolic and diastolic blood pressures (mm Hg) and heart rate (beats/minute) will be measured.

Cerebrospinal fluid biomarkers. Increased CSF protein levels have been detected in pre-symptomatic Krabbe disease patients, with 23 of the 25 (92%) children who underwent lumbar puncture showing elevated CSF protein (Escolar et al., N Engl J Med. 352(20):2069-81, 2005). In this example, CSF will be collected to evaluate biomarkers of myelin integrity. In addition, routine CSF analysis will be performed including cell count, protein determination, glucose, albumin, and IgG. Intactness of the blood-brain barrier is determined by evaluating the relationship between CSF IgG concentrations and serum albumin concentrations. The albumin quotient (AQ) can be estimated to assess the permeability of the blood-brain barrier (AQ=CSF albumin/ serum albumin×100). Intrathecal IgG production is calculated by measuring the CSF IgG/serum albumin ratio, which should be less than 0.27 mg/dl. The IgG index is the ratio of the product of CSF IgG and serum albumin to the product of serum IgG and CSF albumin. An increase in IgG index (>0.70 mg/dl) reflects increased immunoglobulin synthesis in the CNS and is considered to reflect infectious and inflammatory disorders in the CNS. GALC activity in the CSF will also be assessed.

Vector Shedding. Presence of the vector in blood, urine, stool, and saliva following vector administration will be assessed by qPCR.

Safety labs. Clinical chemistry assays on collected blood will be routinely performed to monitor any potential adverse effects. Liver enzymes (aspartate transaminase, alanine transaminase) will be monitored for potential liver toxicity due to GALC overexpression and/or cytotoxic T cell response.

Immune Responses. Whole blood will be collected at baseline and every 3 months post-injection to measure T cell responses against AAVrh.10 and GALC. Plasma or serum will be analyzed to monitor the generation of antibodies against AAVrh.10 at weeks 1, 2, 4, and 8 post-injection, and months 3, 6, 9, and 12.

Brain MRI. Each patient will undergo MRI (i.e., diffusion tensor imaging of the brain). MRI of the brain currently provides the best surrogate structural markers for evaluating myelin disease in Krabbe disease patients (Escolar et al., Am J Neuroradiol. 30(5):1017-21, 2009). The brain MRIs of both control children and patients with Krabbe disease will be visually scored by an experienced neuroradiologist using the modified Loes scoring system, which was developed specifically to monitor disease progression in Krabbe disease patients who underwent with unrelated UCBT (Provenzale et al., Ann NY Acad Sci. 1064:220-9, 2005, Provenzale et al., Am J Roentgenol. 192(1):59-65, 2009). In recent years, diffusion tensor imaging has become the modality of choice to investigate white matter pathology in the developing brain and to evaluate both axonal structure and myelination in babies with demyelinating conditions (Escolar et al., Am J Neuroradiol. 30(5):1017-21, 2009, Gupta et al., Neuroimage Clin. 26; 7:792-8, 2014). Using diffusion tensor imaging with tractography, myelin disruption can be quantitated and measured in standard deviations when compared to age- and gender-matched controls.

Nerve conduction velocity studies (sensory and motor nerves). Babies with Krabbe disease have peripheral neuropathy early in the disease progression, and nerve conduction velocities worsen as the disease progresses (Escolar et al., N Engl J Med. 352(20):2069-81, 2005; Escolar et al., Pediatrics, 118(3):e879-89, 2006), resulting in muscle weakness. A neurophysiologist with extensive experience in Krabbe disease will perform this test.

Nerve conduction velocity (NCV), amplitude (AMP), and distal latency (DL) studies will be performed with conventional techniques. For motor nerves, NCV, AMP, and DL will be measured in the median nerve and in the peroneal nerve. If no relevant signal can be generated at baseline in either of these nerves, the ulnar nerve, tibial nerve, or both will also be evaluated at baseline. One nerve in the arm and one in the leg will be selected on the basis of available responses for repeated evaluations. For sensory nerves, DL, NCV, and AMP will be measured in the median nerve and the sural nerve.

Neurodevelopmental function. Neurodevelopmental assessments and their use in the longitudinal study of Krabbe disease have been extensively published (Escolar et al., N Engl J Med. 352(20):2069-81, 2005; Escolar et al., Pediatrics, 118(3):e879-89, 2006; Escolar et al., Lysosomal Storage Dis. 6(3):71-9, 2006; Martin et al., Acta Paediatr Suppl. 97(457):69-75, 2007). The specific assessment tools were chosen to reflect standardized measures of cognitive, language, and motor development in Krabbe disease patients versus that of normal controls.

Growth velocity. Height, weight, and head circumference will be measured to assess growth velocity. Body mass index will be calculated based on the body weight and height.

Mullen Scales of Early Learning. The Mullen scales can be administered to infants and children up to 68 months of age. T-scores, percentile ranks, and age-equivalent scores can be computed separately for the four scales (visual reception, fine motor, expressive language, and receptive language). Assessment of the young child's nonverbal ability level is important for estimating overall development. A psychometrician trained in the clinical assessment of infants and children will administer the test. Age-equivalent scores will be used to track development over time and to compare across tests.

Figure 4:
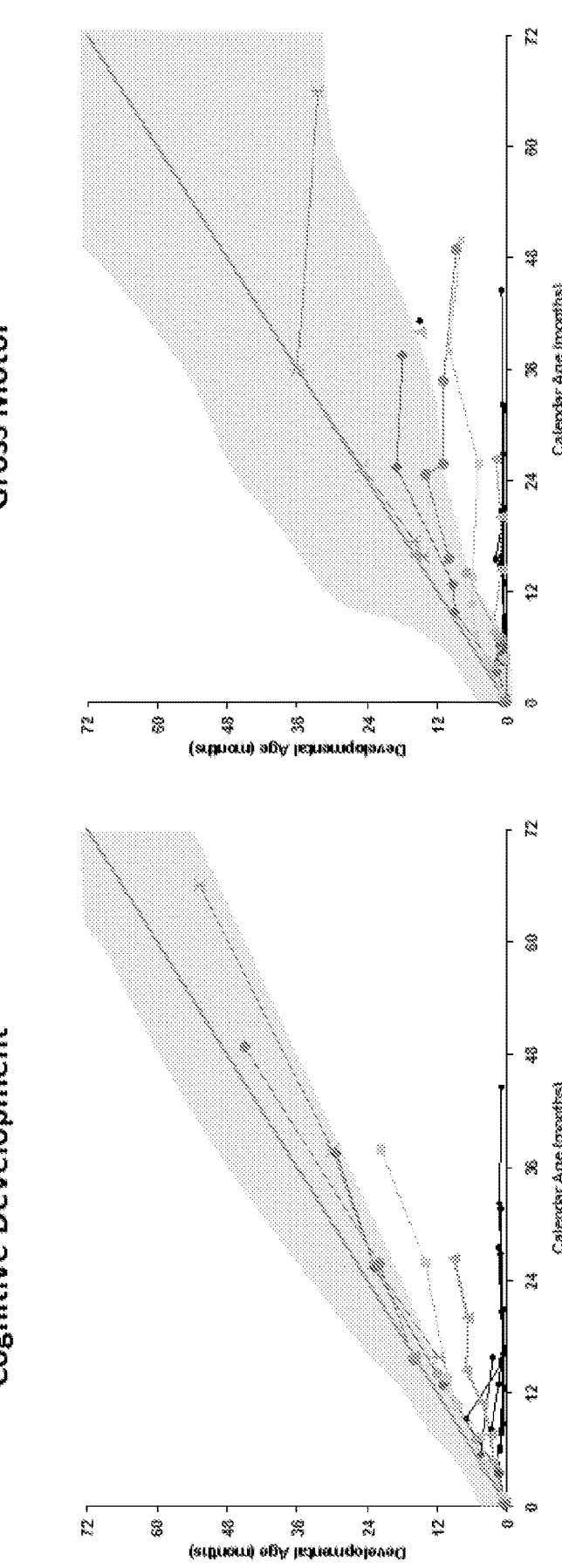
FIG. 4. Neurodevelopmental Outcomes of Children with Krabbe's Disease after Cord-Blood Transplantation. A unique line represents each patient's development. Black lines (bottom) represent symptomatic patients who underwent transplantation as infants, and colored lines represent asymptomatic patients who also underwent transplantation as infants. The green diagonal line represents typical development of unaffected children. The shaded area indicates the variability in typical development of unaffected children. From Escolar et al., *NEJM,* 352:2069-81, 2005.

Peabody Developmental Motor Scales. The Peabody scales capture both quantitative and qualitative abilities on some items, increasing the sensitivity to changing motor patterns as the children's disease progresses or during recovery. FIG. 4 shows an example of the trajectories of individual patients treated with unrelated UCBT using the tools mentioned above (Escolar et al., N Engl J Med. 352(20): 2069-81, 2005). FIG. 4 is an example of trajectories of individual patients transplanted with unrelated umbilical cord blood and tested with the tools presented above. The colored lines show the development of the asymptomatic or minimally symptomatic patients. The black lines represent patients transplanted after significant symptoms. The trajectories of the symptomatic patients is similar to those of who are untreated.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

---

We claim:

1. A method of treating Krabbe disease in a human subject, comprising:

immunosuppressing the human subject;

administering a therapeutically effective amount of human umbilical cord blood to the human subject; and administering a therapeutically effective amount of a nucleic acid molecule encoding galactocerebrosidase (GALC) to the human subject, wherein the nucleic acid molecule encodes a GALC protein comprising at least 95% sequence identity to SEQ ID NO: 2 or 6, and wherein the umbilical cord blood is administered at least 3 weeks prior to the nucleic acid molecule encoding GALC.

2. The method of claim 1, wherein the nucleic acid molecule encoding GALC comprises at least 95% sequence identity to SEQ ID NO: 1.

3. The method of claim 1, wherein the nucleic acid molecule encodes a GALC protein comprising at least 95% sequence identity to SEQ ID NO: 2.

4. The method of claim 1, wherein the nucleic acid molecule encoding GALC is operably linked to a promoter.

5. The method of claim 1, wherein the nucleic acid molecule encoding GALC is administered intravenously.

6. The method of claim 1, wherein the nucleic acid molecule encoding GALC is part of a vector.

7. The method of claim 6, wherein the vector is a viral vector.

8. The method of claim 7, wherein the viral vector is an adeno-associated vector (AAV).

9. The method of claim 8, wherein the adeno-associated vector is AAV serotype rh.10.

10. The method of claim 7, wherein the viral vector is administered at a dose of at least $2\times10^{13}$ genome copies (gc) per subject or at least $2\times10^{14}$ gc per subject.

11. The method of claim 1, wherein the umbilical cord blood is allogenic to the subject.

12. The method of claim 1, wherein administering a therapeutically effective amount of umbilical cord blood comprises administering a total nucleated cell dose of at least $3\times10^{7}$/kg to the subject.

13. The method of claim 1, wherein immunosuppressing the subject comprises administering a therapeutically effective amount of alemtuzumab, hydroxyurea, fludarabine, and busulfan.

14. The method of claim 1, wherein immunosuppressing the subject further comprises administering a therapeutically effective amount of tacrolimus and mycophenolate mofetil (MMF).

15. The method of claim 1, wherein the Krabbe disease is infantile Krabbe disease.

16. The method of claim 1, wherein the nucleic acid molecule encoding GALC comprises at least 98% sequence identity to SEQ ID NO: 1.

17. The method of claim 1, wherein the nucleic acid molecule encoding GALC comprises at least 99% sequence identity to SEQ ID NO: 1.

18. The method of claim 1, wherein the nucleic acid molecule encoding GALC comprises SEQ ID NO: 1.

19. The method of claim 1, wherein the nucleic acid molecule encodes a GALC protein comprising at least 98% sequence identity to SEQ ID NO: 2.

20. The method of claim 1, wherein the nucleic acid molecule encodes a GALC protein comprising at least 99% sequence identity to SEQ ID NO: 2.

21. The method of claim 1, wherein the nucleic acid molecule encodes a GALC protein comprising SEQ ID NO: 2.

22. The method of claim 1, wherein immunosuppressing the subject comprises administering a therapeutically effective amount of alemtuzumab, hydroxyurea, fludarabine, melphalan and thiotepa.

23. The method of claim 1, wherein the nucleic acid molecule encodes a GALC protein comprising at least 97% sequence identity to SEQ ID NO: 2.

24. The method of claim 1, wherein the nucleic acid molecule encodes a GALC protein comprising SEQ ID NO: 2 with 1-20 deletions and 2 amino acid changes.

25. The method of claim 24, wherein the nucleic acid molecule encodes a GALC protein comprising SEQ ID NO: 2 with 1-5 amino acid substitutions.

26. The method of claim 24, wherein the nucleic acid molecule encodes a GALC protein comprising SEQ ID NO: 2 with 2 amino acid substitutions.

27. The method of claim 1, wherein the nucleic acid molecule encodes a GALC protein comprising at least 95% sequence identity to SEQ ID NO: 6.

28. The method of claim 1, wherein the nucleic acid molecule encodes a GALC protein comprising at least 97% sequence identity to SEQ ID NO: 6.

29. The method of claim 1, wherein the nucleic acid molecule encodes a GALC protein comprising at least 98% sequence identity to SEQ ID NO: 6.

30. The method of claim 1, wherein the nucleic acid molecule encodes a GALC protein comprising at least 99% sequence identity to SEQ ID NO: 6.

31. The method of claim 1, wherein the nucleic acid molecule encodes a GALC protein comprising SEQ ID NO: 6.

32. The method of claim 1, wherein the nucleic acid molecule encodes a GALC protein comprising SEQ ID NO: 6 with 1-5 amino acid substitutions.

33. The method of claim 32, wherein the nucleic acid molecule encodes a GALC protein comprising SEQ ID NO: 6 with 2 amino acid substitutions.

34. The method of claim 1, wherein the nucleic acid molecule encoding GALC comprises at least 95% sequence identity to SEQ ID NO: 5.

35. The method of claim 1, wherein the nucleic acid molecule encoding GALC comprises at least 97% sequence identity to SEQ ID NO: 5.

36. The method of claim 1, wherein the nucleic acid molecule encoding GALC comprises at least 98% sequence identity to SEQ ID NO: 5.

37. The method of claim 1, wherein the nucleic acid molecule encoding GALC comprises at least 99% sequence identity to SEQ ID NO: 5.

38. The method of claim 1, wherein the nucleic acid molecule encoding GALC comprises SEQ ID NO: 5.

39. The method of claim 1, wherein the GALC protein retains the ability to remove galactose from ceramide derivatives.

* * * * *